(12) United States Patent
Salafsky et al.

(10) Patent No.: US 11,486,881 B2
(45) Date of Patent: Nov. 1, 2022

(54) METHODS AND DEVICES FOR DETECTION OF PERIPHERAL MEMBRANE PROTEIN INTERACTIONS USING NONLINEAR OPTICAL TECHNIQUES

(71) Applicant: Quanta Therapeutics, Inc., San Francisco, CA (US)

(72) Inventors: Joshua S. Salafsky, San Francisco, CA (US); Carl Benton Moree, III, Redwood City, CA (US)

(73) Assignee: QUANTA THERAPEUTICS, INC., San Francisco, CA (US)

( * ) Notice: Subject to any disclaimer, the term of this patent is extended or adjusted under 35 U.S.C. 154(b) by 879 days.

(21) Appl. No.: 16/184,513

(22) Filed: Nov. 8, 2018

(65) Prior Publication Data

US 2019/0137510 A1 May 9, 2019

Related U.S. Application Data

(63) Continuation of application No. PCT/US2017/031820, filed on May 9, 2017.

(60) Provisional application No. 62/333,447, filed on May 9, 2016.

(51) Int. Cl.
| | |
|---|---|
| *C12M 1/34* | (2006.01) |
| *G01N 33/68* | (2006.01) |
| *G01N 33/543* | (2006.01) |
| *G01N 33/542* | (2006.01) |

(52) U.S. Cl.
CPC ........... *G01N 33/6845* (2013.01); *C12M 1/34* (2013.01); *G01N 33/542* (2013.01); *G01N 33/543* (2013.01); *G01N 2500/00* (2013.01); *G01N 2500/04* (2013.01)

(58) Field of Classification Search
None
See application file for complete search history.

(56) References Cited

U.S. PATENT DOCUMENTS

| | | |
|---|---|---|
| 5,156,810 A | 10/1992 | Ribi |
| 5,498,538 A | 3/1996 | Kay et al. |
| 6,228,326 B1 | 5/2001 | Boxer et al. |
| 6,456,423 B1 | 9/2002 | Nayfeh et al. |
| 6,699,719 B2 | 3/2004 | Yamazaki et al. |
| 6,953,694 B2 | 10/2005 | Salafsky et al. |
| 7,045,337 B2 | 5/2006 | Schultz et al. |
| 7,108,970 B2 | 9/2006 | Levinson |
| 7,336,359 B1 | 2/2008 | Simpson et al. |
| 7,470,549 B2 | 12/2008 | Yamamoto et al. |
| 7,485,424 B2 | 2/2009 | Korlach et al. |
| 7,518,764 B2 | 4/2009 | Osborne et al. |
| 7,545,494 B2 | 6/2009 | Haiml et al. |
| 7,545,501 B2 | 6/2009 | Muraishi et al. |
| 7,563,624 B2 | 7/2009 | Ezoe et al. |
| 8,139,288 B2 | 3/2012 | Osborne et al. |
| 8,497,073 B2 | 7/2013 | Salafsky |
| 8,932,822 B1 | 1/2015 | Salafsky |
| 9,182,406 B2 | 11/2015 | Salafsky |
| 9,383,361 B2 | 7/2016 | Salafsky |
| 9,395,358 B2 | 7/2016 | Salafsky |
| 9,428,789 B2 | 8/2016 | Salafsky et al. |
| 9,880,172 B2 | 1/2018 | Salafsky |
| 9,938,560 B2 | 4/2018 | Salafsky et al. |
| 9,989,534 B2 | 6/2018 | Salafsky et al. |
| 10,451,630 B2 | 10/2019 | Salafsky et al. |
| 10,672,502 B2 | 6/2020 | Salafsky |
| 10,768,174 B2 | 9/2020 | Salafsky |
| 2002/0094528 A1 | 7/2002 | Salafsky |
| 2002/0127563 A1 | 9/2002 | Salafsky |
| 2003/0148391 A1 | 8/2003 | Salafsky |
| 2004/0146460 A1 | 7/2004 | Salafsky |
| 2005/0118731 A1 | 6/2005 | Salafsky |
| 2006/0063188 A1 | 3/2006 | Zanni et al. |
| 2006/0228725 A1 | 10/2006 | Salafsky |
| 2012/0202296 A1 | 8/2012 | Eisenthal |
| 2013/0129628 A1 | 5/2013 | Pantazis et al. |
| 2013/0288271 A1 | 10/2013 | Salafsky et al. |
| 2014/0178896 A1 | 6/2014 | Salafsky |
| 2014/0178897 A1 | 6/2014 | Salafsky |
| 2014/0186854 A1 | 7/2014 | Salafsky |
| 2014/0187431 A1 | 7/2014 | Salafsky |
| 2014/0187432 A1 | 7/2014 | Salafsky |
| 2014/0187433 A1 | 7/2014 | Salafsky |
| 2015/0051110 A1* | 2/2015 | Salafsky ................ C07K 14/82 506/11 |
| 2015/0330990 A1 | 11/2015 | Salafsky et al. |
| 2016/0292354 A1 | 10/2016 | Salafsky |
| 2016/0356767 A1 | 12/2016 | Salafsky |
| 2016/0356768 A1 | 12/2016 | Salafsky |
| 2017/0350883 A1 | 12/2017 | Salafsky |
| 2018/0217150 A1 | 8/2018 | Salafsky |
| 2018/0340940 A1 | 11/2018 | Salafsky et al. |
| 2020/0064354 A1 | 2/2020 | Salafsky et al. |

FOREIGN PATENT DOCUMENTS

| | | |
|---|---|---|
| CA | 2604099 C | 2/2011 |
| CN | 1864066 A | 11/2006 |

(Continued)

OTHER PUBLICATIONS

Sly et al (Anal. Chem. 86:11045-54 supporting information) (Year: 2014).*
Winter et al (J. Med. Chem. 58:2265-74) (Year: 2015).*
Genbank accession No. NP_005624 (Year: 2001).*
EP17796718.9 Office Action dated Feb. 15, 2021.
Co-pending U.S. Appl. No. 16/850,374, inventors Salafsky; Joshua et al., filed Apr. 16, 2020.
Berkovic, et al. Interference between second-harmonic generation from a substrate and from an adsorbate layer. Journal of the Optical Society of America B-Optical Physics. 1989; 6:205-208.
Bethea. Experimental technique of de induced SHG in liquids: measurement of the nonlinearity of CH2I2. Applied Optics. 1975; 14:1447-1451.

(Continued)

*Primary Examiner* — Christopher M Gross
(74) *Attorney, Agent, or Firm* — Wilson Sonsini Goodrich & Rosati

(57) ABSTRACT

Methods and devices for identifying agents that block binding or activation of peripheral membrane proteins are disclosed.

18 Claims, 18 Drawing Sheets

(56) References Cited

FOREIGN PATENT DOCUMENTS

| | | |
|---|---|---|
| CN | 101738462 A | 6/2010 |
| EP | 0740156 A1 | 10/1996 |
| EP | 0740156 B1 | 9/2001 |
| EP | 0941474 B1 | 3/2006 |
| EP | 1798555 A1 | 6/2007 |
| EP | 3161168 A1 | 5/2017 |
| GB | 2520111 A | 5/2015 |
| GB | 2538216 A | 11/2016 |
| JP | H11119270 A | 4/1999 |
| JP | 2003344404 A | 12/2003 |
| JP | 2004521323 A | 7/2004 |
| JP | 2004530105 A | 9/2004 |
| WO | WO-9005317 A1 | 5/1990 |
| WO | WO-9709446 A1 | 3/1997 |
| WO | WO-9820036 A1 | 5/1998 |
| WO | WO-0244412 A1 | 6/2002 |
| WO | WO-0246764 A1 | 6/2002 |
| WO | WO-02054071 A1 | 7/2002 |
| WO | WO-02061415 A1 | 8/2002 |
| WO | WO-02095070 A2 | 11/2002 |
| WO | WO-03055379 A2 | 7/2003 |
| WO | WO-03064991 A2 | 8/2003 |
| WO | WO-03104851 A2 | 12/2003 |
| WO | WO-2011140030 A2 | 11/2011 |
| WO | WO-2012129347 A1 | 9/2012 |
| WO | WO-2013115867 A1 | 8/2013 |
| WO | WO-2013162654 A1 | 10/2013 |
| WO | WO-2014201435 A1 | 12/2014 |
| WO | WO-2016003936 | 1/2016 |
| WO | WO-2016106286 A1 | 6/2016 |
| WO | WO-2016161386 A1 | 10/2016 |
| WO | WO-2017196891 A1 | 11/2017 |
| WO | WO-2018204135 A2 | 11/2018 |

OTHER PUBLICATIONS

Bouevitch, et al. Probing membrane potential with nonlinear optics. Biophys J. Aug. 1993;65(2):672-9.

Campagnola, et al. High-resolution nonlinear optical imaging of live cells by second harmonic generation. Biophys J. Dec. 1999;77(6):3341-9.

Campagnola, et al. Second-harmonic imaging microscopy for visualizing biomolecular arrays in cells, tissues and organisms. Nat Biotechnol. Nov. 2003;21(11):1356-60. Published online Oct. 31, 2003; doi:10.1038/nbt894.

Campagnola, et al. Three-dimensional high-resolution second-harmonic generation imaging of endogenous structural proteins in biological tissues. Biophysical Journal. 2002; 81:493-508.

Chen, et al. Detection of Molecular Monolayers by Optical Second-Harmonic Generation. Physical Review Letters. 1981; 46:1010-1012.

Clancy et al. Second-harmonic phase determination by real-time in situ interferometry. Phys Chem Chem Phys 19:3722-3728 (2017). DOI: 10.1039/C6CP07708K.

Clark, et al. Second harmonic generation properties of fluorescent polymer-encapsulated gold nanoparticles. J. Am. Chem. Soc. 2000; 122:10234-10235.

Clays, et al. Nonlinear optical properties of proteins measured by hyper-rayleigh scattering in solution. Science. Nov. 26. 1993;262(5138):1419-22.

Cohen, et al. A Fluorescent Probe Designed for Studying Protein Conformational Change. PNAS. 2005; 102(4):965-970.

Cohen, et al. Probing protein electrostatics with a synthetic fluorescent amino acid. Science. 2002;296:1700-1703.

Conboy, et al. Studies of Alkane/water interfaces by total internal reflection second harmonic generation. J. Phys. Chem. 1994; 98:9688-9698.

Co-pending U.S. Appl. No. 10/484,658, filed Jul. 17, 2002.
Co-pending U.S. Appl. No. 11/002,620, filed Dec. 2, 2004.
Co-pending U.S. Appl. No. 15/211,859, filed Jul. 15, 2016.
Co-pending U.S. Appl. No. 16/452,045, filed Jun. 25, 2019.
Co-pending U.S. Appl. No. 16/668,279, filed Oct. 30, 2019.
Co-pending U.S. Appl. No. 16/797,480, filed Feb. 21, 2020.

Ditcham, et al. An immunosensor with potential for the detection of viral antigens in body fluids, based on surface second harmonic generation. Biosens Bioelectron. May 2001;16(3):221-4.

Dworczak, et al. Electric field induced second harmonic generation (EFISH) experiments in the swivel cell: new aspects of an established method. Phys. Chem. Chem. Phys., 2000; 2:5057-5064.

Eisenthal. Photochemistry and photophysics of liquid interfaces by second harmonic spectroscopy. J. Phys. Chem. 1996; 100:12997-13006.

EP17796718.9 Extended European Search Report dated Nov. 5, 2019.

Fejer, et al. Quasi-Phase-Matched Second Harmonic Generation Tuning And Tolerances. IEEE Journal Of Quantum Electronics. 1992; 28(11):2631-2654.

Felderhof, et al. Optical second-harmonic generation from adsorbate layers in total-reflection geometry. Journal of the Optical Society of America B-Optical Physics. 1993; 10:1824-1833.

Feller, et al. Investigation of surface-induced alignment liquid-crystal molecules by optical second-harmonic generation. Physical Review A. 1991; 43(12), 6778-6792.

Fittinghoff. Collinear type II second-harmonic-generation frequency-resolved optical gating for use with high-numerical-aperature objectives, 1998, Opt Lett, 23(13), 1046-1048.

Galletto, et al. Enhancement of second harmonic response by adsorbates on gold colloids: the effect of aggregation. J. Phys. Chem. B. 1999; 103:8706-8710.

Goh, et al. Absolute Orientation of Water-Molecules at the Neat Water-Surface. Journal of Physical Chemistry. 1988; 92:5074-5075.

Groves, et al. Micropatterning fluid bilayers on solid supports. Science. 1997; 275:651-653.

Han et al. Different Interfacial Behaviors of Peptides Chemically Immobilized on Surfaces with Different Linker Lengths and via Different Termini. J Phys Chem 118:2904-2912 (Feb. 20, 2014). DOI: dx.doi.org/10.1021/jp4122003.

Heinz. Determination of molecular orientation of monolayer adsorbates by optical second-harmonic generation. Physical Review A. 1983; 28(3):1883-1885.

Heinz, et al. Spectroscopy of Molecular Monolayers by Resonant Second-Harmonic Generation. Phys. Rev. Lett. 1982; 48, 478. DOI: http://dx.doi.org/10.1103/PhysRevLett.48.478.

Heinz. Second-Order Nonlinear Optical Effects at Surfaces and Interfaces. Chapter 5 of Nonlinear Surface Electromagnetic Phenomena. Edited by H. E. Ponath and G. I. Stegeman. pp. 353-416 (1991).

Kajikawa, et al. Second harmonic generation in disperse-red-labeled poly(methyl methacrylate) Langmuir Blodgett film. Appl. Phys. Letters. May 3, 1993; 62(18):2161-2163.

Kang, et al. Specific adsorption of histidine-tagged proteins on silica surfaces modified with Ni2+/NTA-derivatized poly(ethylene glycol). Langmuir. May 22, 2007;23(11):6281-8. Epub Apr. 20, 2007.

Kemnitz, et al. The Phase of 2nd-Harmonic Light Generated at an Interface and Its Relation to Absolute Molecular-Orientation. Chemical Physics Letters. 1986; 131:285-290.

Khatchatouriants, et al. GFP is a selective non-linear optical sensor of electrophysiological processes in Caenorhabditis elegans. Biophys J. Nov. 2000;79(5):2345-52.

Kriech, et al. Using the intrinsic chirality of a molecule as a label-free probe to detect molecular adsorption to a surface by second harmonic generation. Applied Spectroscopy. 2005; 59:46-753.

Levine, et al. Charge transfer complexes and hyperpolarizabilities. J. Chem. Phys. 1977; 66:1070-1074.

Levine, et al. Second and third order hyperpolarizabilities of organic molecules. J. Chem. Phys. 1975; 63(6):2666-2682.

Levine, et al. Second Order Hyperpolarizability of a Polypeptide a-helix: Poly—y-benzyl-L-glutamate. J. Chem. Phys. 1976; 65(5):1989-1993.

Lewis, et al. Second Harmonic Generation of Biological Interfaces: Probing the Membrane Protein Bacteriorhodopsin and Imaging

(56) References Cited

OTHER PUBLICATIONS

Membrane Potential Around GFP Molecules at Specific Sites in Neuronal Cells of C. elegans. Chemical Physics. 1999; 245:133-144.
Matar, et al. Second Harmonic Generation, a new approach for analyzing the interfacial properties of a short tryptophan-rich peptide. Chemical Physics Letters. vol. 500, pp. 161-166, (2010).
McGuinness, et al. Direct, Real-time Detection of Protein Conformation: Revealing Therapeutic Opportunities Using Second Harmonic Generation (SHG) Detection. Biodesy, LLC. Poster M143. Mar. 18-21, 2011.
Millard, et al. Second harmonic imaging microscopy. Methods Enzymol. 2003;361:47-69.
MJFF. Development of modulators of alpha-synuclein conformation for PD therapeutics. MJFF grant abstract. 2008.
MJFF. Development of Potent Conformation-Specific Compounds Directed to Monomeric Alpha-Synuclein. MJFF grant abstract. 2009.
MJFF. Development of SHG to Discover Drugs to Selectively Block Alphas toxicity. MJFF grant abstract. 2007.
MJFF. Partnering program. Organization and team overview. 2009.
Moreaux, et al. Membrane imaging by second harmonic generation microscopy. Journal of Optical Society of America B: Optical Physics. 2000; 17(10):1685-1694.
Moree, et al. Protein Conformational Changes Are Detected and Resolved Site Specifically by Second-Harmonic Generation. Biophys J. Aug. 18, 2015;109(4):806-15. doi: 10.1016/j.bpj.2015.07.016.
Moree, et al. Small Molecules Detected by Second-Harmonic Generation Modulate the Conformation of Monomeric α-Synuclein and Reduce Its Aggregation in Cells. J Biol Chem. Nov. 13, 2015;290(46):27582-93. doi: 10.1074/jbc.M114.636027. Epub Sep. 22, 2015.
NSF. SBIR Phase I: Development of a Conformational Screen for Rapidly Identifying Kinase Inhibitor Type Using SHG. NSF SBIR grant abstract. 2011.
NSF. SBIR Phase I: Development of a Conformational Screen for Rapidly Identifying Kinase Inhibitor Type Using SHG. NSF SBIR grant abstract. 2012.
NSF. SBIR Phase II: Development of an SHG Instrument, Artemis QuantTM, for measuring conformational change in real time. NSF SBIR grant abstract. 2013.
Nye, et al. Kinetic control of histidine-tagged protein surface density on supported lipid bilayers. Langmuir. Apr. 15, 2008;24(8):4145-9. doi: 10.1021/la703788h. Epub Feb. 28, 2008.
Ong, et al. Polarization of water molecules at a charged interface: second harmonic studies of the silica/water interface. Chemical Physics Letters. 1992; 191:327-335.
Oral Abstracts from the Society of Biomolecular Sciences 14th Annual Conference and Exhibition: St. Louis, Missouri Apr. 6-10, 2008. J. Biomol Screen 2008 13: 697. DOI: 10.1177/1087057108322219.
Paszti, et al. Sum frequency generation vibrational spectroscopy studies of protein adsorption on oxide-covered Ti surfaces. Journal of Physical Chemistry B. 2004; 108:7779-7787.
Peleg, et al. Nonlinear optical measurement of membrane potential around single molecules at selected cellular sites. Proc Natl Acad Sci USA. Jun. 8, 1999;96(12):6700-4.
Pitchford, et al. Direct, Real-time Detection of Kinase Type II Inhibitors Using Second Harmonic Generation (SHG) Detection. Biodesy, LLC. Poster T380. Mar. 17, 2011.
Polizzi, et al. (2004). Ellipsometric approach for the real-time detection of label-free protein adsorption by second harmonic generation. Journal of the American Chemical Society. 2004; 126:5001-5007.
Reider, et al. Second-order Nonlinear Optical Effects at Surfaces and Interfaces: recent advances. In Electromagnetic Waves: Recent Developments in Research, vol. 2, Photonic Probes of Surfaces. Halevia, P., editor. Elsevier Science, Amsterdam. Chapter 9. 1995. 415-478.
Reider et al. Coherence artifacts in second harmonic microscopy. Applied Physics B: Lasers & Optics. 68(3):343-347 (1999).
Rinuy, et al. Second harmonic generation of glucose oxidase at the air/water interface. Biophysical Journal. 1999; 77:3350-3355.
Salafsky. Detection of protein conformational change by optical second-harmonic generation. J Chem Phys. Aug. 21, 2006;125(7):074701.
Salafsky, et al. A second-harmonic-active unnatural amino acid as a structural probe of biomolecules on surfaces. J. Phys. Chem. B, 2008, 112 (47), pp. 15103-15107.
Salafsky, et al. Architecture and function of membrane proteins in planar supported bilayers: A study with photosynthetic reaction centers' Biochemistry. 1996; 35(47):14773-14781.
Salafsky, et al. Protein absorption at interfaces detected by second-harmonic generation. J. Phys. Chem. B. 2004; 108(10):3376. Additions and Corrections.
Salafsky, et al. Protein absorption at interfaces detected by second-harmonic generation. Journal of Physical Chemistry B. 2000; 104:7752-7755.
Salafsky, et al. Real-time measurement of protein conformational change in key therapeutic targets: application to Abl kinase and mutant Ras. Biodesy, Llc. SLAS2012 talk abstract. Nov. 2011.
Salafsky, et al. Second Harmonic Spectroscopy: Detection and Orientation of Molecules at a Biomembrane Interface. Chemical Physics Letters 2000; 319:435-439.
Salafsky, et al. SHG labels for detection of molecules by second harmonic generation. Chemical Physics Letters. 2001; 342:485-491.
Salafsky, J. (Apr. 2008). "Second-Harmonic Generation (SHG) for Identification of Allosteric D & Conformation-Specific Compounds" PowerPoint Presentation presented to SBS, 30 pages.
Salafsky, J. (Apr. 15, 2009). "Detection Method for Conformational Change Second-Harmonic Generation Provides a Molecular-Level, Functional Readout in Real Time" Gen Eng & Biotech News, 2 pages.
Salafsky. Real-time detection of GPCR conformational change. NIH grant abstract. 2005-2007.
Salafsky. Real-time measurement of protein conformational change in key therapeutic targets: applications to Abl-kinase and mutant Ras. Biodesy, LLC. SLAS Conference. PPT presentation. Feb. 7, 2012.
Salafsky. Second-harmonic generation as a probe of conformational change in molecules. Chemical Physics Letters. 2003; 381(5):705-709.
Salafsky. Second-harmonic generation for studying structural motion of biological molecules in real time and space. Phys Chem Chem Phys. Nov. 14, 2007;9(42):5704-11. Epub Sep. 7, 2007.
Salafsky. Second-Harmonic Generation (SHG) for Identification of Allosteric and Conformation-Specific Compounds. Journal of Biomolecular Screening. 2008; 13(7):697.
Salafsky. SHG for integrin receptor drug discovery. NIH grant abstract. 2006-2007.
Shen. Optical Second Harmonic Generation at Interfaces. Annual Review of Physical Chemistry. 1989; 40(1):327-350.
Shen.. Surface properties probed by second-harmonic and sum-frequency generation. Nature. 1989; 337: 20 519-525.
Shen. The Principles of Nonlinear Optics, John Wiley & Sons, New York. 1984.
Sigal, et al. A self-assembled monolayer for the binding and study of histidine-tagged proteins by surface plasmon resonance. Anal Chem. Feb. 1, 1996;68(3):490-7.
Simpson et al. An SHG Magic Angle: Dependence of Second Harmonic Generation Orientation Measurements on the Width of the Orientation Distribution. J Am Chem Soc 21(11):2635-2636 (Mar. 6, 1999). DOI: https://doi.org/10.1021/ja983683f.
Singer, et al. Measurements of molecular second-order optical susceptibilities using dc-induced second harmonic generation. J. Chem. Phys. 1981; 75:3572-3580.
Sly et al. Determination of Multivalent Protein-Ligand Binding Kinetics by Second-Harmonic Correlation Spectroscopy. Anal Chem 26:11045-11054 (Oct. 14, 2014).
Tom, et al. Development of modulators of alpha-synuclein conformation for Parkinson's disease therapeutics. Biodesy, LLC. Max Planck Institute for Biophysical Chemistry. MJFF poster. Oct. 2010.

(56) References Cited

OTHER PUBLICATIONS

Vanzi, et al., Protein conformation and molecular order probed by second-harmonic-generation microscopy, Journal of Biomedical Optics, Jun. 18, 2012, 17(6):060901, 8 Pages.

Wang, et al. In situ, nonlinear optical probe of Surfactant Adsorption on the Surface of Microparticles in Colloids. Langmuir 2000, 16, 2475-2481.

Wang, et al. Polarity of liquid interfaces by second harmonic generation spectroscopy, 1997, J Phys Chem A, 101, 713-718.

Wartchow, et al. Assaying protein conformational change in real time—A novel approach for target-based drug discovery. Biodesy, LLC. SLAS2012 Roche poster. Feb. 6-8, 2012.

Weidner, et al. Sum frequency generation and solid-state NMR study of the structure, orientation, and dynamics of polystyrene-adsorbed peptides. Proc Natl Acad Sci USA. Jul. 27, 2010;107(30):13288-93. doi: 10.1073/pnas.1003832107. Epub Jul. 13, 2010.

Yang, et al. Surface second harmonic generation (SSHG)—a new scheme for immunoassay. Proceedings of the SPIE. 1996; 2676:290-296. http://dx.doi.org/10.1117/12.238808.

Zhuang, et al. Mapping molecular orientation and conformation at interfaces by surface nonlinear optics. Physical Review B. 1999; 59(19):12632-12640.

\* cited by examiner

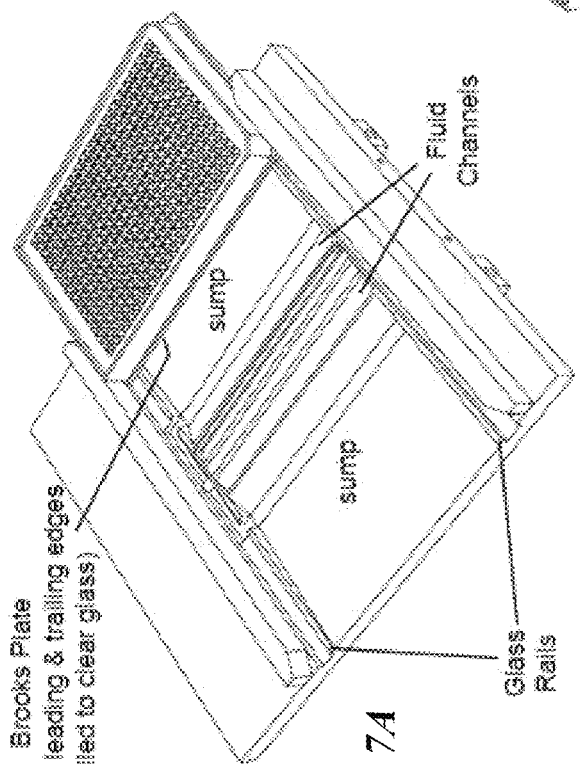
FIG. 7A
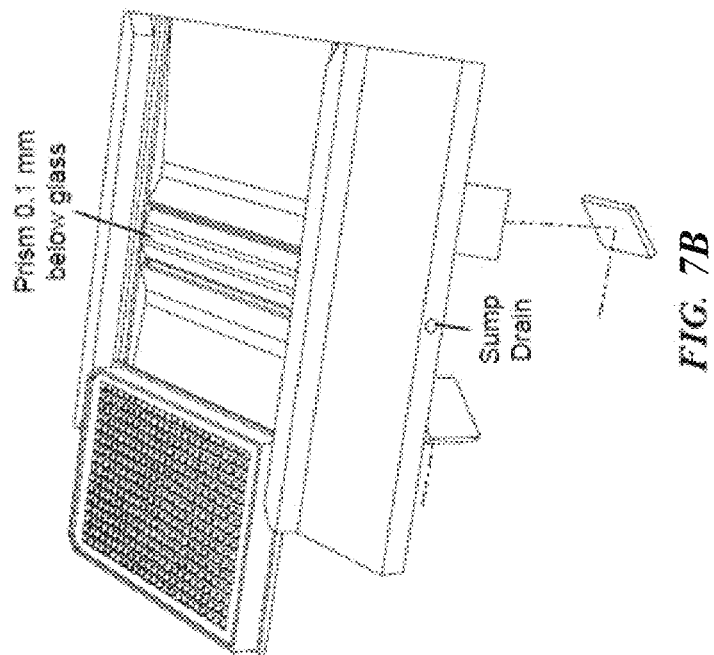
FIG. 7B
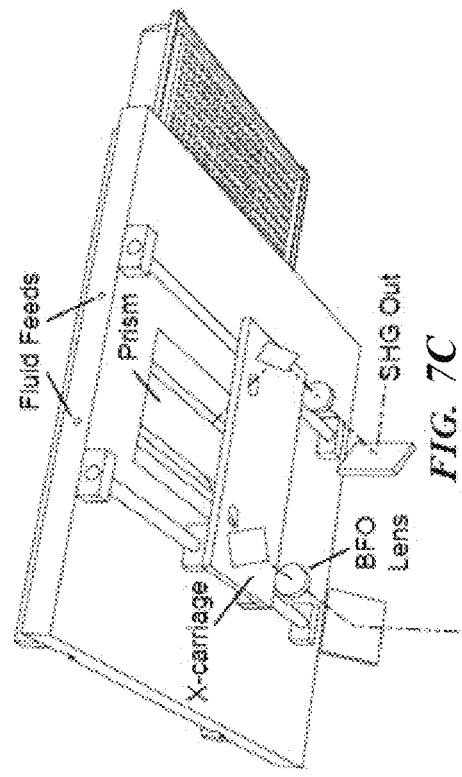
FIG. 7C
FIG. 7

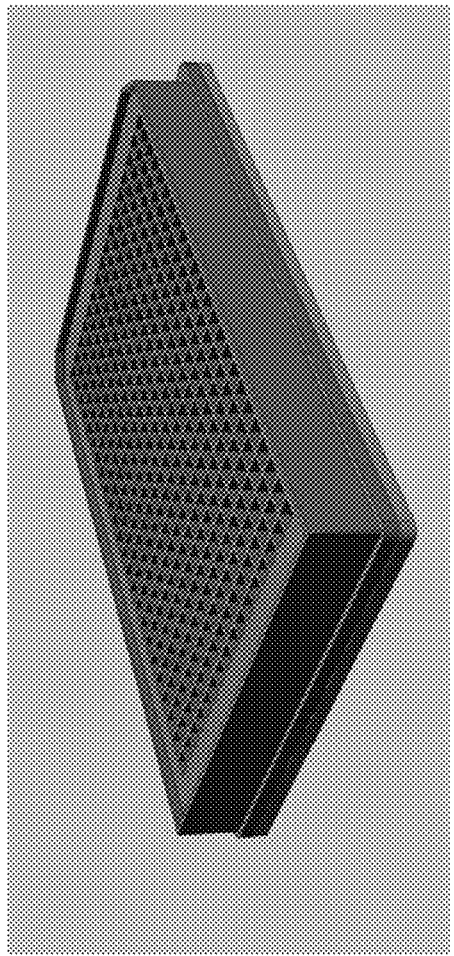
FIG. 9A
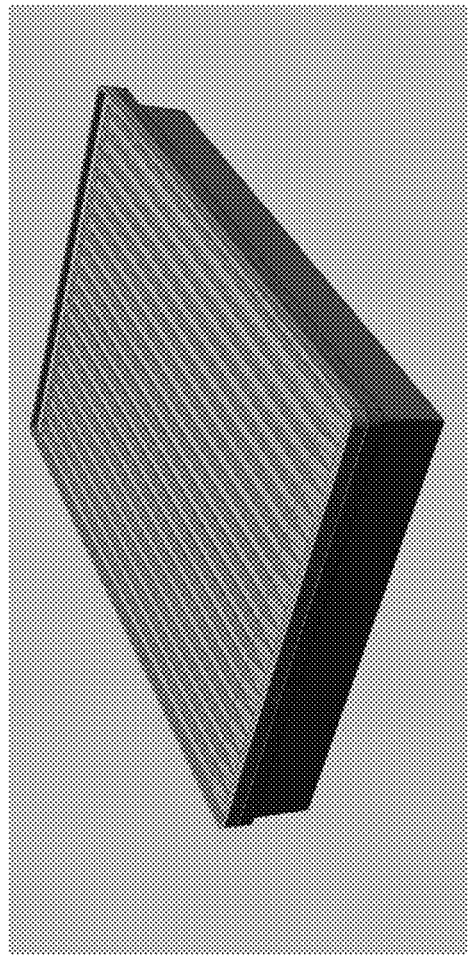
FIG. 9B
FIG. 9

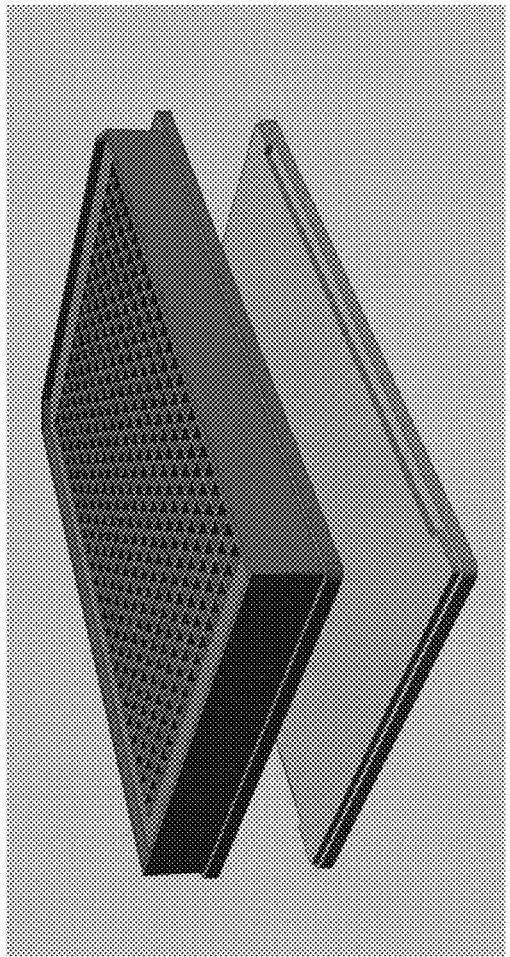
FIG. 10A
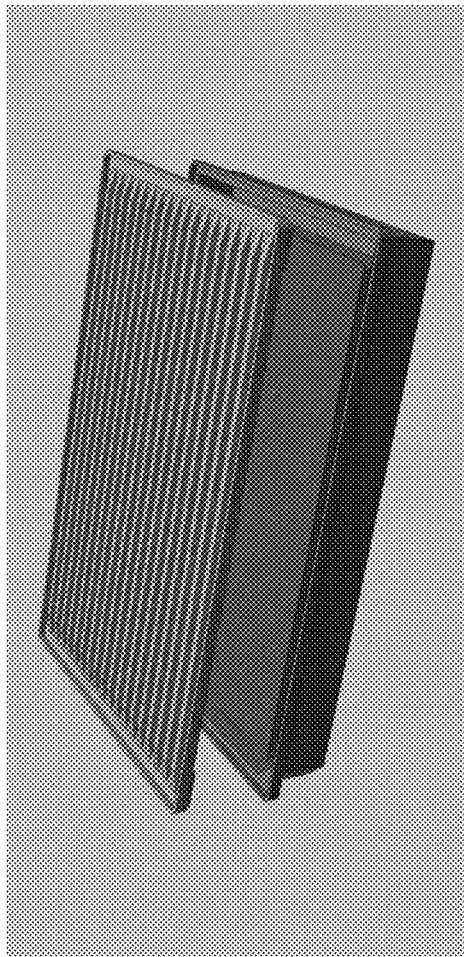
FIG. 10B
FIG. 10

METHODS AND DEVICES FOR DETECTION OF PERIPHERAL MEMBRANE PROTEIN INTERACTIONS USING NONLINEAR OPTICAL TECHNIQUES

CROSS-REFERENCE

This application is a Continuation Application of International Patent Application PCT PCT/US2017/031820, filed May 9, 2017, which claims the benefit of U.S. Provisional Application No. 62/333,447, filed on May 9, 2016, each of which is incorporated herein by reference in its entirety.

BACKGROUND

Peripheral membrane proteins bind transiently to biological membranes through specific or nonspecific interactions with membrane proteins and lipids. They are known to play an important role in a number of cell signaling and membrane transport pathways. Categories of peripheral membrane proteins include peripheral enzymes (e.g. phospholipases, cholesterol oxidases, glycosyltransferase) involved in the metabolism of membrane components, peripheral enzymes (e.g. protein kinase C) involved in cell signaling pathways, cytoskeletal proteins (e.g. spectrin and actin in erythrocytes), transporters of small hydrophobic molecules (e.g. glycolipid transfer proteins, sterol carrier proteins, and phosphatidylinositol transfer proteins), electron carrier proteins (e.g. cytochrome C, cupredoxins, adrenodoxin reductase, and some flavoproteins) which participate in electron transport, and polypeptide hormones and toxins (e.g. scorpion venom, snake venom, and bacterial toxins). The regulatory protein subunits of many transmembrane receptors and ion channel proteins are also peripheral membrane proteins.

Peripheral membrane proteins bind to biological membrane components through a variety of molecular interactions, including electrostatic interactions, hydrogen bonding, and/or van der Waals interactions with integral membrane proteins or directly with the lipid bilayer via interactions with polar lipid head groups. They are released from biological membranes by rinsing with a high ionic strength or alkaline buffer, and will typically be collected with the water-soluble fraction in a protein extraction and purification procedure. In some cases, the binding interactions between peripheral membrane proteins and membrane components are directed by peripheral protein domains that target specific membrane lipid components, e.g., diacylglycerol or phosphoinositides, or specific membrane protein components [Stehelin (2009), "Lipid Binding Domains: More Than Simple Lipid Effectors", J. Lipid Research, April Supplement, S299-S304; Moravcevic, et al. (2012), "Conditional Peripheral Membrane Proteins: Facing Up to Limited Specificity", Structure 20(1): 15-27]. Examples of such protein domains include the C1 and C2 domains of protein kinase C (PKC) which bind to diacylglycerol, the PH (pleckstrin homology) domain which binds to phosphatidylinositol-4,5-bisphosphate (PtdIns(4,5)P2), and the PX (Phox homology) and FYVE (Fab1, YOTB, Vac1, EEA1) domains which both bind to the endosomal phosphoinositide PtdIns3P. Additional examples include the ENTH domain (binds PtdIns(4,5)P2; involved in cytoskeletal processes and endocytosis), the ANTH domain (binds to PtdIns(4,5)P2; universal adaptor for nucleation of clathrin coats), the BAR domain (binds preferentially to curved membrane regions), the FERM domain (found in cytoskeletal proteins), the PDZ domain (involved in anchoring membrane receptor proteins to cytoskeletal components), and Tubby domains (bind to phosphatidylinositol). In some cases, peripheral membrane proteins include structural domains that confer their membrane binding specificity. Examples include annexin, synapsin I, synuclein, the gamma-carboxyglutamate (GLA)-domains of blood coagulation components, and the cytoskeletal proteins spectrin and α-actinin-2. The binding of annexin or GLA-domains to the phosphate groups of membrane lipids is mediated by calcium ions ($Ca^{2+}$).

Reversible interactions between peripheral membrane proteins and cellular membrane components have been shown to regulate a variety of cell signaling and membrane transport processes. Regulatory switches that control the membrane affinity of peripheral membrane proteins include modulation of the membrane lipid composition, and modification of the peripheral protein itself by ligand binding, phosphorylation, or acylation [Johnson, et al., (2002), "Amphitropic Proteins: Regulation by Reversible Membrane Interactions (Review)", Mol. Membr. Biol. 16(3):217-35]. Membrane binding, in turn, may modulate the peripheral protein's function by co-localizing the protein with a substrate, activator, or other downstream target. For example, the close proximity of membrane-associated peripheral enzyme proteins with membrane protein or lipid molecules that constitute their substrates facilitates the enzymatic reactions that play a key role in a number of cell signaling pathways [Ghosh, et al. (2006), "Properties of Group IV Phospholipase A2 Family (Review)", Prog. Lipid. Res. 45(6):487-510]. Binding of peripheral proteins to membrane components may also promote conformational changes within peripheral protein structural domains, resulting in activation of their biological function [Johnson, et al., (2002), "Amphitropic Proteins: Regulation by Reversible Membrane Interactions (Review)", Mol. Membr. Biol. 16(3):217-35; Guruvasuthevan, et al. (2006), "Evidence that Membrane Insertion of the Cytosolic Domain of Bcl-xL is Governed by an Electrostatic Mechanism". J. Mol. Biol. 359 (4): 1045-1058].

Because of their involvement in the regulation of cell signaling and membrane transport phenomena, peripheral membrane proteins constitute potential targets for the development of new therapeutic drugs for a variety of diseases, e.g., abnormal synuclein function may be associated with Parkinson's disease and Alzheimer's disease. Hence there is a need for assay technologies that may be utilized for high throughput screening of compound libraries to identify new drug candidates, and for follow-up testing as lead candidate molecules progress through the medicinal chemistry-based optimization process.

As described more fully below, second harmonic generation (SHG) is a nonlinear optical process which may be configured as a surface-selective detection technique to enable detection of conformational change in proteins and other biological targets (as described previously, for example, in U.S. Pat. Nos. 6,953,694, 8,497,073, and U.S. Pat. No. 9,182,406). Disclosed herein are devices and methods for performing nonlinear-optical detection of the activation or inhibition of peripheral membrane protein binding interactions and/or activation or inhibition of peripheral membrane protein conformational changes upon binding to a membrane bilayer component or test agent.

SUMMARY

Disclosed herein are methods for detecting binding of a candidate peripheral membrane protein to a supported membrane, the methods comprising: a) providing a substrate having a first substrate surface comprising a supported membrane, wherein the supported membrane comprises one or more lipid or protein components; b) contacting the supported membrane with the candidate peripheral membrane protein, wherein the candidate peripheral membrane protein is labeled with a nonlinear-active label; c) illuminating the first substrate surface with excitation light of at least one fundamental frequency, wherein the excitation light is provided by at least one light source; and d) detecting light generated by the nonlinear-active label as a result of the illumination in step c) both before and after contacting the supported membrane with the candidate peripheral membrane protein, wherein a change in a physical property of the light detected before and after contacting the supported membrane with the candidate peripheral membrane protein indicates that the candidate peripheral membrane protein binds to the supported membrane or a component thereof.

Disclose herein are methods for identifying a test agent that modulates a change in a binding property or a conformational state of a peripheral membrane protein, the methods comprising: a) providing a substrate having a first substrate surface comprising a supported membrane, wherein the supported membrane comprises one or more lipid or protein components; b) contacting the supported membrane with the peripheral membrane protein, wherein the peripheral membrane protein binds to the supported membrane and is labeled with a first nonlinear-active label; c) illuminating the first substrate surface with excitation light of at least one fundamental frequency, wherein the excitation light is provided by at least one light source; and d) detecting light generated by the first nonlinear-active label as a result of the illumination in step c) both before and after contacting the bound peripheral membrane protein with the test agent, wherein a change in a physical property of the light detected upon contacting the peripheral membrane protein with the test agent indicates that the test agent modulates a change in the binding of the peripheral membrane protein to the supported membrane or a change in the conformational state of the peripheral membrane protein. In some embodiments, the peripheral membrane protein is labeled with a second nonlinear-active label attached to a site that does not undergo a conformational change, and wherein a detected change in light generated by the second nonlinear-active label upon illumination with excitation light of an appropriate fundamental frequency upon contacting the peripheral membrane protein with the test agents indicates that the conformational state of the peripheral membrane protein induced by the test agent results in release of the peripheral membrane protein from the supported membrane.

Disclosed herein are methods for identifying a test agent that modulates binding of a peripheral membrane protein to a supported membrane, the methods comprising: a) providing a substrate having a first substrate surface comprising a supported membrane, wherein the supported membrane comprises one or more lipid or protein components; b) sequentially contacting the supported membrane with the peripheral membrane protein in the presence and in the absence of the test agent, wherein the peripheral membrane protein is labeled with a nonlinear-active label; c) illuminating the first substrate surface with excitation light of at least one fundamental frequency, wherein the excitation light is provided by at least one light source; and d) detecting light generated by the nonlinear-active label as a result of the illumination in step c) both in the presence and in the absence of the test agent, wherein a change in a physical property of the light detected in the presence and in the absence of the test agent indicates that the test agent modulates binding of the peripheral membrane protein to the supported membrane.

Disclosed herein are methods for identifying an agent B that binds to an allosteric site on a peripheral membrane protein conformation, the methods comprising: a) contacting the peripheral membrane protein with an agent A that binds to an active site of the peripheral membrane protein or wherein agent A is naturally bound to the active site of the peripheral membrane protein when isolated, and wherein the peripheral membrane protein is attached to a supported membrane; b) contacting the peripheral membrane protein with the agent B, wherein the peripheral membrane protein is labeled with a nonlinear-active label having a net orientation at an interface, wherein a detectable signal is generated by the nonlinear-active label using a surface selective technique, and wherein the detectable signal indicates a conformational change in the structure of the peripheral membrane protein produced when the agent B binds to an allosteric site on the peripheral membrane protein; and c) measuring the presence or absence of the detectable signal after the peripheral membrane protein has been contacted with the agent B.

In some embodiments, the supported membrane comprises a supported lipid bilayer. In some embodiments, the methods further comprise adjusting the relative percentages of two or more lipid components in the supported lipid bilayer to enhance the degree of binding of the peripheral membrane protein to the supported lipid bilayer. In some embodiments, the supported membrane comprises an artificial membrane. In some embodiments, the artificial membrane has been modified by attachment of one or more lipid, protein, or membrane protein components. In some embodiments, the light generated by the nonlinear-active label is coherent. In some embodiments, the excitation light and the light generated by the nonlinear-active label have well-defined phase relationships. In some embodiments, the nonlinear-active label comprises a second harmonic-active, sum frequency-active, or difference frequency-active label. In some embodiments, the one or more nonlinear-active labels are nonlinear-active unnatural amino acids that have been incorporated into the peripheral membrane protein. In some embodiments, the first substrate surface comprises an array of supported lipid bilayers or artificial membranes localized in discrete regions of the first substrate surface. In some embodiments, two or more supported lipid bilayers or artificial membranes of the array of supported lipid bilayers comprise the same bound peripheral membrane protein. In some embodiments, two or more supported lipid bilayers or artificial membranes of the array of supported lipid bilayers comprise different bound peripheral membrane proteins. In some embodiments, the array of supported lipid bilayers or artificial membranes is configured in a microwell plate format. In some embodiments, the microwell plate format is a 96-well, 384-well, or 1536-well format. In some embodiments, the discrete regions of the first substrate surface are sequentially illuminated using total internal reflection of the excitation light by adjusting the position of the substrate relative to the at least one light source. In some embodiments, each discrete region of the first substrate surface is optically coupled with a second substrate surface that is parallel to the first substrate surface and that comprises an array of entrance and exit prisms, and wherein the entrance and exit prisms for a given discrete region are different from each other and are not aligned directly opposite the discrete region. In some embodiments, one or more lipid components of a supported lipid bilayer or artificial membrane comprise lipids selected from the group consisting of diacylglycerol, phosphatidic acid (PA), phosphatidylethanolamine (PE), phosphatidylcholine (PC), phosphatidylserine (PS), phosphatidylinositol (PI), phosphatidylinositol phosphate (PIP), phosphatidylinositol biphosphate (PIP2), phosphatidylinositol triphosphate (PIP3), ceramide phosphorylcholine (sphingomyelin; SPH), ceramide phosphorylethanolamine (sphingomyelin; Cer-PE), ceramide phosphoryllipid, cholesterol, or any combination thereof. In some embodiments, one or more protein components of a supported lipid bilayer or an artificial membrane comprise proteins or subdomains thereof selected from the group consisting of G-protein coupled receptors (GPCRs), transmembrane receptors, receptor tyrosine kinases, ion channel proteins, cytochrome P450 enzymes (CYPs), transport proteins, photosynthetic reaction centers, lipid-anchored proteins, or any combination thereof. In some embodiments, the physical property of the detected light is selected from the group consisting of intensity, wavelength, polarization, the time-course of the intensity, the time-course of the wavelength, the time-course of the polarization, or any combination thereof. In some embodiments, the substrate is fabricated from glass, fused-silica, a polymer, or any combination thereof. In some embodiments, the peripheral membrane protein or a subdomain thereof is selected from the group consisting of extracellular matrix proteins, protein kinases, transmembrane receptor regulatory proteins, ion channel regulatory proteins, cytochrome proteins, lipid-anchored proteins, or any combination thereof. In some embodiments, the peripheral membrane protein is a protein comprising a subdomain selected from the group consisting of C1 domains, C2 domains, PH domains, PX domains, Fab1 domains, YOTB domains, Vac1 domains, EEA1 domains, FYVE domains, ENTH domains, ANTH domains, BAR domains, FERM domains, PDZ domains, Tubby domains, or any combination thereof. In some embodiments, the test agent, agent A, or agent B is selected from the group consisting of proteins, peptides, receptors, enzymes, antibodies, DNA, RNA, oligonucleotides, lipid molecules, small molecules, and carbohydrates, or any combination thereof. In some embodiments, the peripheral membrane protein is contacted with the test agent prior to or simultaneously with contacting the supported lipid bilayer or artificial membrane with the peripheral membrane protein. In some embodiments, the peripheral membrane protein is contacted with the test agent after contacting the supported lipid bilayer or artificial membrane with the peripheral membrane protein. In some embodiments, the methods further comprise comparing the change in a physical property of the detected light observed upon contacting the peripheral membrane protein with a test agent to that observed upon contacting the peripheral membrane protein with a control. In some embodiments, one or more lipid components or one or more protein components of the supported lipid bilayer or artificial membrane are also labeled with a nonlinear-active label. In some embodiments, one or more lipid components or one or more protein components are labeled with a nonlinear-active label that is the same as that used to label the peripheral membrane protein. In some embodiments, one or more lipid components or one or more protein components are labeled with a nonlinear-active label that is different from that used to label the peripheral membrane protein.

Also disclosed herein are devices comprising: a) a substrate, the substrate comprising: i) an M×N array of discrete regions formed on a surface of the substrate, wherein M is the number of rows of discrete regions and N is the number of columns of discrete regions in the array, and each discrete region comprises a supported lipid bilayer or artificial membrane, wherein the supported lipid bilayer or artificial membrane comprises one or more lipid or protein components, and wherein each discrete region optionally further comprises a peripheral membrane protein; and ii) an R×S array of prisms integrated with the substrate and optically coupled to the discrete regions, wherein R is the number of rows of prisms and S is the number of columns of prisms in the array; wherein R=M+2 and S=N, or R=M and S=N+2.

In some embodiments, each of the discrete regions is optically coupled with at least one input prism and at least one output prism, and wherein the input prism and the output prism are spatially distinct. In some embodiments, M=8 and N=12. In some embodiments, M=16 and N=24. In some embodiments, M=32 and N=48. In some embodiments, M is greater than 4 and N is greater than 4. In some embodiments, the device further comprises a well-forming component bonded to a top surface of the substrate in order to isolate each discrete region in a separate well. In some embodiments, each of the discrete regions comprises an area of up to about 100 mm$^2$. In some embodiments, each discrete region or well is located directly above a single prism of the array of prisms integrated with the substrate. In some embodiments, the substrate is composed of glass, fused-silica, a polymer, or any combination thereof. In some embodiments, one or more lipid components comprise lipids selected from the group consisting of diacylglycerol, phosphatidic acid (PA), phosphatidylethanolamine (PE), phosphatidylcholine (PC), phosphatidylserine (PS), phosphatidylinositol (PI), phosphatidylinositol phosphate (PIP), phosphatidylinositol biphosphate (PIP2), phosphatidylinositol triphosphate (PIP3), ceramide phosphorylcholine (sphingomyelin; SPH), ceramide phosphorylethanolamine (sphingomyelin; Cer-PE), ceramide phosphoryllipid, cholesterol, or any combination thereof. In some embodiments, one or more protein components comprise proteins or subdomains thereof selected from the group consisting of G-protein coupled receptors (GPCRs), transmembrane receptors, receptor tyrosine kinases, ion channel proteins, cytochrome P450 enzymes (CYPs), transport proteins, photosynthetic reaction centers, lipid-anchored proteins, or any combination thereof. In some embodiments, the optional peripheral membrane protein or a subdomain thereof is selected from the group consisting of extracellular matrix proteins, protein kinases, transmembrane receptor regulatory proteins, ion channel regulatory proteins, cytochrome proteins, lipid-anchored proteins, or any combination thereof. In some embodiments, the optional peripheral membrane protein is a protein comprising a subdomain selected from the group consisting of C1 domains, C2 domains, PH domains, PX domains, Fab1 domains, YOTB domains, Vac1 domains, EEA1 domains, FYVE domains, ENTH domains, ANTH domains, BAR domains, FERM domains, PDZ domains, Tubby domains, or any combination thereof.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in their entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 7A-C show different views of one exemplary design concept for a system that uses a continuously recirculating flow of index-matching fluid to provide high optical coupling efficiency between the prism (attached to the optical instrument in this example) and the substrate (configured as the transparent bottom of a microwell plate in this example). The substrate (microwell plate) is free to translate relative to the prism while a continuous flow of index-matching fluid provided by the indicated fluid channels ensures good optical coupling of excitation light with the substrate. FIG. 7A: top-front axonometric view. FIG. 7B: top-rear axonometric view. FIG. 7C: bottom-front axonometric view.

FIGS. 9A-B illustrate a microwell plate with integrated prism array for providing good optical coupling of the excitation light to the top surface of the substrate. Such a device may be useful in conducting high-throughput screening of drug candidates that target peripheral membrane proteins. FIG. 9A: top axonometric view. FIG. 9B: bottom axonometric view.

FIGS. 10A-B show exploded views of the microwell plate device shown in FIGS. 9A-B. FIG. 10A: top axonometric view. FIG. 10B: bottom axonometric view.

DETAILED DESCRIPTION

Figure 1:
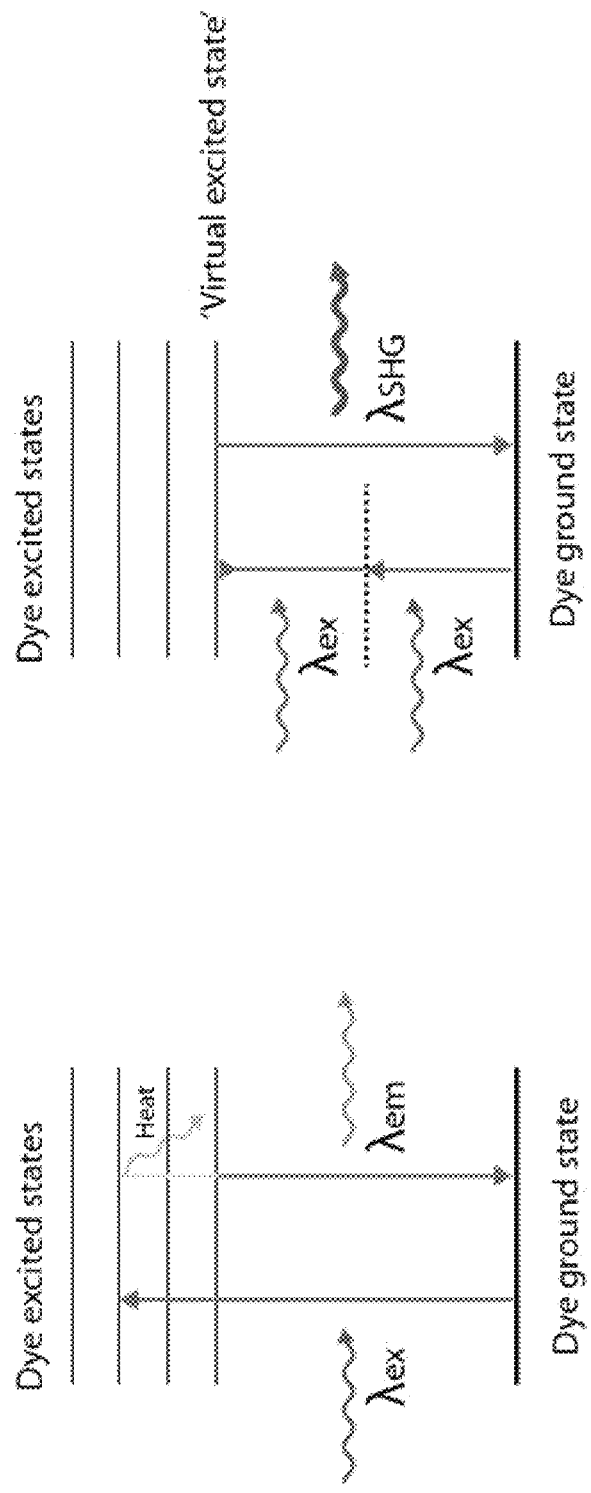
FIG. 1A provides a schematic illustration of the energy level diagrams for fluorescence (an absorption process).
FIG. 1B provides a schematic illustration of the energy level diagrams for second harmonic generation (a two photon scattering process).

Disclosed herein are methods and systems for performing nonlinear-optical detection of peripheral membrane protein binding interactions and conformational changes. In some embodiments, the methods and systems described provide for the use of nonlinear-optical techniques to detect activation or inhibition of peripheral membrane protein conformational changes upon binding to a membrane protein or lipid molecule. In some embodiments, the methods and systems described provide for the use of nonlinear-optical techniques to detect activation or inhibition of peripheral membrane protein conformational changes upon binding of a test agent or a control. In some embodiments, the methods and systems described provide for high throughput analysis of binding interactions and conformational change in peripheral membrane proteins, and screening of libraries of test agents to identify agents that block binding of peripheral membrane proteins to membrane proteins or membrane lipids. In some embodiments, the screening methods disclosed herein may be directed towards identifying agents that induce conformational change (or block conformational change) in peripheral membrane proteins or membrane proteins upon binding. As used herein, "high throughput" refers to the ability to perform rapid analysis of conformation or conformational change for a large plurality of peripheral membrane proteins or other biological entities optionally contacted with one or more test entities, or to the ability to perform rapid analysis of conformation or conformational change for one or more peripheral membrane proteins or other biological entities optionally contacted with a large plurality of test entities, or to any combination of these two modalities.

In some embodiments of the present disclosure, systems and methods are described for determining orientation, conformation, or changes in orientation or conformation of peripheral membrane proteins in response to contacting the peripheral membrane proteins with one or more test entities. As used herein, determining orientation, conformation, or changes thereof may involve measurement of a nonlinear optical signal which is related to and/or proportional to the average orientation of a nonlinear-active label or tag. In general, the systems and methods disclosed rely on the use of second harmonic generation (SHG) or related nonlinear optical techniques for detection of orientation, conformation, or conformational change, as described previously, for example, in U.S. Pat. Nos. 6,953,694, and 8,497,073.

As used herein, the phrase "nonlinear optical technique" includes second harmonic generation, sum frequency generation, and/or difference frequency generation. Sum frequency generation is a nonlinear optical technique wherein two photons of different excitation wavelength or frequency interact with a nonlinear material and are re-emitted as a single photon having an energy equal to the sum of that for the two excitation photons, i.e. having a frequency equal to the sum of the two excitation frequencies. Difference frequency generation is a nonlinear optical technique wherein two photons of different excitation wavelength or frequency interact with a nonlinear material and are re-emitted as a single photon having an energy equal to the difference of that for the two excitation photons, i.e. having a frequency equal to the difference of the two excitation frequencies.

As used herein, the phrase "nonlinear-active" refers to molecules, labels, or tags that are second harmonic-active, sum frequency-active, or difference frequency-active, i.e. that are capable of generating second harmonic light, sum frequency light, or difference frequency light respectively upon exposure to light of the appropriate wavelengths, intensities, and phases.

Detection of Conformation Using Second Harmonic Generation

Second harmonic generation, in contrast to the more widely used fluorescence-based techniques (FIG. 1A), is a nonlinear optical process, in which two photons of the same excitation wavelength or frequency interact with a nonlinear material and are re-emitted as a single photon having twice the energy, i.e. twice the frequency and half the wavelength, of the excitation photons (FIG. 1B). Second harmonic generation only occurs in nonlinear materials lacking inversion symmetry (i.e. in non-centrosymmetric materials), and requires a high intensity excitation light source. It is a special case of sum frequency generation, and is related to other nonlinear optical phenomena such as difference frequency generation.

Second harmonic generation and other nonlinear optical techniques can be configured as surface-selective detection techniques because of their dependence on the orientation of the nonlinear-active species. Tethering of the nonlinear-active species to a surface, for example, can instill an overall degree of orientation that is absent when molecules are free to undergo rotational diffusion in solution. An equation commonly used to model the orientation-dependence of nonlinear-active species at an interface is:

$$\chi^{(2)} = N_s \langle \alpha^{(2)} \rangle$$

where $\chi^{(2)}$ is the nonlinear susceptibility, $N_s$ is the total number of nonlinear-active molecules per unit area at the interface, and $\langle \alpha^{(2)} \rangle$ is the average orientation of the nonlinear hyperpolarizability ($\alpha^{(2)}$) of these molecules. The intensity of SHG is proportional to the square of the nonlinear susceptibility, and is thus dependent on both the number of oriented nonlinear-active species at the interface and to changes in their average orientation.

Second harmonic generation and other nonlinear optical techniques may be rendered additionally surface selective through the use of total internal reflection as the mode for delivery of the excitation light to the optical interface on which nonlinear-active species have been immobilized. Total internal reflection of the incident excitation light creates an "evanescent wave" at the interface, which may be used to selectively excite only nonlinear-active labels that are in close proximity to the surface, i.e. within the spatial decay distance of the evanescent wave, which is typically on the order of tens of nanometers. Total internal reflection may also be used to excite fluorescence in a surface-selective manner, for example to excite a fluorescence donor attached to the optical interface, which then transfers energy to a suitable acceptor molecule via a fluorescence resonance energy transfer (FRET) mechanism. In the present disclosure, the evanescent wave generated by means of total internal reflection of the excitation light is preferentially used to excite a nonlinear-active label or molecule. The efficiency of exciting nonlinear active species will depend strongly on both their average orientation and on their proximity to the interface.

Figure 2:
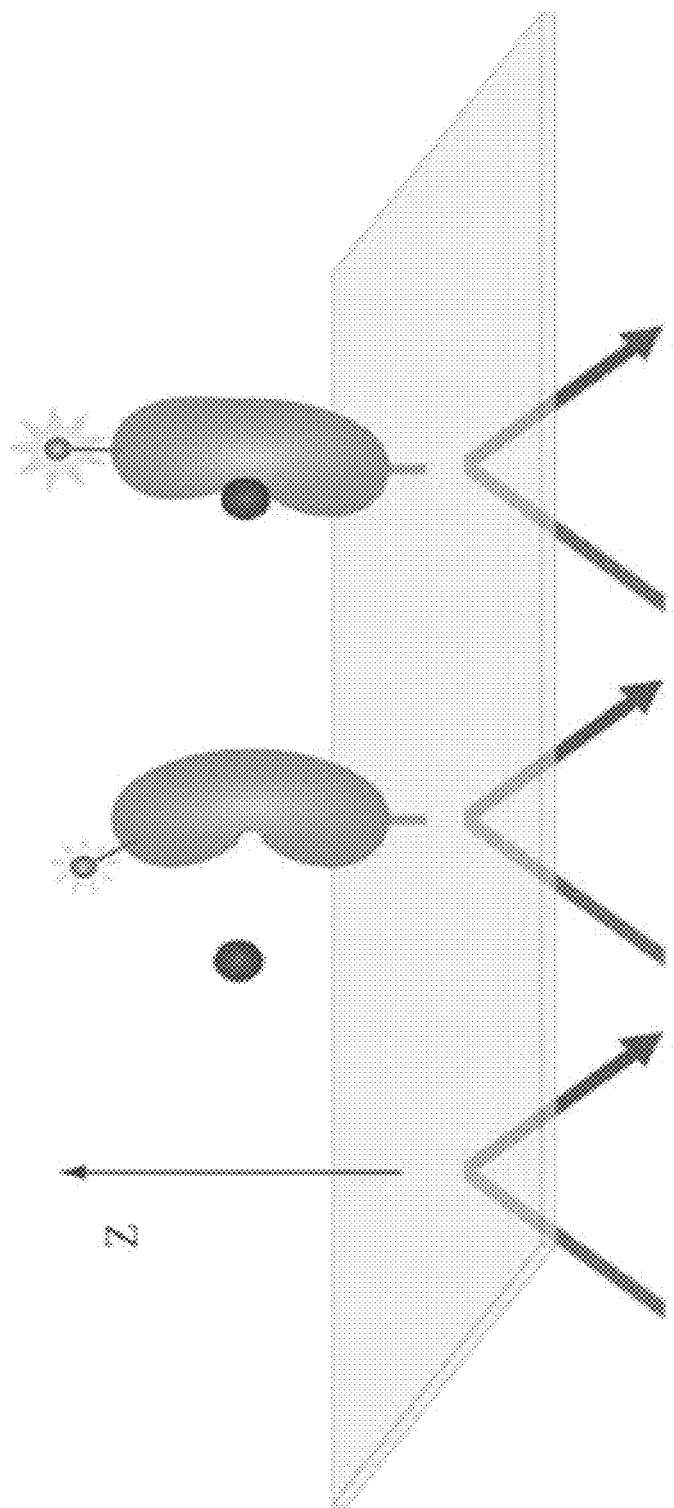
FIG. 2 provides a schematic illustration of a conformational change in a protein (labeled with a nonlinear-active tag) which is induced by binding of a ligand, and its impact on the distance and/or orientation of a nonlinear-active label relative to an optical interface to which the protein is attached.

This surface selective property of SHG and other nonlinear optical techniques can be exploited to determine average orientation or to detect conformational change in biological molecules immobilized at interfaces. For example, conformational change in a receptor molecule due to binding of a ligand, might be detected using a nonlinear-active label or moiety wherein the label is attached to or associated with the receptor such that the conformational change leads to a change in the orientation or distance of the label with respect to the interface (FIG. 2), and thus to a change in a physical property of the nonlinear optical signal. Historically, the use of surface-selective nonlinear optical techniques has been confined mainly to applications in physics and chemistry, since relatively few biological samples are intrinsically non-linearly active. Recently, the use of second harmonic active labels ("SHG labels") has been introduced, allowing virtually any molecule or particle to be rendered highly non-linear active. The first example of this was demonstrated by labeling the protein cytochrome c with an oxazole dye and detecting the protein conjugate at an air-water interface with second harmonic generation [Salafsky, J., "'SHG-labels' for Detection of Molecules by Second Harmonic Generation", Chem. Phys. Lett. 342(5-6):485-491 (2001)].

Surface-selective nonlinear optical techniques are also coherent techniques, meaning that the fundamental and nonlinear optical light beams have wave fronts that propagate through space with well-defined spatial and phase relationships. The use of surface-selective nonlinear optical detection techniques for analysis of conformation of biological molecules or other biological entities has a number of inherent advantages over other optical approaches, including: i) sensitive and direct dependence of the nonlinear signal on the orientation and/or dipole moment(s) of the nonlinear-active species, thereby conferring sensitivity to conformational change; (ii) higher signal-to-noise (lower background) than fluorescence-based detection since the nonlinear optical signal is generated only at surfaces that create a non-centrosymmetric system, i.e. the technique inherently has a very narrow "depth-of-field"; (iii) as a result of the narrow "depth of field", the technique is useful when measurements must be performed in the presence of a overlaying solution, e.g. where a binding process might be obviated or disturbed by a separation or rinse step. This aspect of the technique may be particularly useful for performing equilibrium binding measurements, which require the presence of bulk species, or kinetics measurements where the measurements are made over a defined period of time; (iv) the technique exhibits lower photobleaching and heating effects than those that occur in fluorescence, due to the facts that the two-photon absorption cross-section is typically much lower than the one-photon absorption cross-section for a given molecule, and that SHG (and sum frequency generation or difference frequency generation) involves scattering, not absorption; (v) minimal collection optics are required and higher signal to noise is expected since the fundamental and nonlinear optical beams (e.g., second harmonic light) have well-defined incoming and outgoing directions with respect to the interface. This is particularly advantageous compared to fluorescence-based detection, as fluorescence emission is isotropic and there may also be a large fluorescence background component to detected signals arising from out-of-focal plane fluorescent species.

Peripheral Membrane Protein Assays

In some embodiments of the present disclosure, SHG or related nonlinear optical techniques are used to detect binding interactions between peripheral membrane proteins and membrane components or other biological entities. In some embodiments of the present disclosure, SHG and related nonlinear optical techniques are used to detect binding interactions between a candidate peripheral membrane protein and lipid or protein components of a lipid bilayer or membrane to determine if the candidate peripheral protein is in fact a peripheral protein. In some embodiments of the present disclosure, SHG or related nonlinear optical techniques are used to detect conformational changes in peripheral membrane proteins upon binding to membrane proteins or membrane lipids. In some embodiments of the present disclosure, SHG or related nonlinear optical techniques are used to detect conformational changes in peripheral membrane proteins upon binding of a ligand, test agent, or control. In some embodiments of the present disclosure, SHG or related nonlinear optical techniques are used to identify allosteric modulators of peripheral membrane proteins. In some embodiments of the present disclosure, SHG or related nonlinear optical techniques are used to detect conformational changes in membrane proteins upon binding of peripheral membrane proteins.

In many of these embodiments, peripheral membrane proteins are immobilized (or tethered, or attached) in an oriented fashion on a substrate that comprises an optical interface. Immobilization can be accomplished through any of a variety of immobilization chemistries known to those of skill in the art, as discussed in more detail below. In preferred embodiments, peripheral membrane proteins may be attached to the substrate via covalent or non-covalent interactions with protein or lipid components of a supported lipid bilayer (FIG. 3), the latter comprising small patches of lipid bilayer confined to a silicon or glass surface by means of hydrophobic and electrostatic interactions, where the bilayer is "floating" above the substrate surface on a thin layer of aqueous buffer. Methods of preparing supported lipid bilayers are well known in the art. See, for example, Castellana, E., and Cremer, P., (2006), "Solid Supported Lipid Bilayers: From Biophysical Studies to Sensor Design", Surface Science Reports, 61(10):429-444.

As used herein, the term "peripheral membrane protein" (or "peripheral protein") refers to proteins that are reversibly associated with lipid bilayers or biological membranes. Peripheral membrane proteins typically bind to biological membrane components through any of a variety of molecular interactions, including electrostatic interactions, hydrogen bonding, and/or van der Waals interactions with integral membrane proteins or directly with the lipid bilayer via interactions with polar lipid head groups. Examples of peripheral membrane protein categories include, but are not limited to, peripheral enzymes, cytoskeletal proteins, transporters of small hydrophobic molecules, electron carrier proteins which participate in electron transport, and polypeptide hormones and toxins. The regulatory protein subunits of many transmembrane receptors and ion channel proteins are also peripheral membrane proteins. In some embodiments, peripheral membrane proteins may be lipid-anchored proteins, i.e., proteins associated with the surface of the lipid bilayer or biological membrane that are covalently attached to lipid molecules embedded within the bilayer or membrane. Examples include, but are not limited to, prenylated proteins, fatty acylated proteins, or glycosylphosphatidylinositol (GPI) proteins. In some embodiments, the disclosed methods may be used to determine if a candidate peripheral membrane protein, e.g., a protein which is suspected to be a peripheral membrane protein or is suspected to interact with other membrane proteins, is in fact a peripheral membrane protein. The term "peripheral membrane protein" may thus encompass both known and candidate peripheral membrane proteins, and may also include mutant forms of both known and candidate peripheral membrane proteins.

As used herein, the term "membrane protein" (or "integral membrane protein") refers to proteins that are irreversibly associated with lipid bilayers or biological membranes. Typically, membrane proteins are at least partially embedded within the hydrophobic core of the lipid bilayer or membrane. Examples of membrane proteins include, but are not limited to, G-protein coupled receptors (GPCRs), transmembrane receptors, receptor tyrosine kinases, ion channel proteins, cytochrome P450 enzymes (CYPs), transport proteins, or photosynthetic reaction centers, or subdomains thereof. In some embodiments, lipid-anchored proteins may also be considered membrane proteins.

Figure 3:
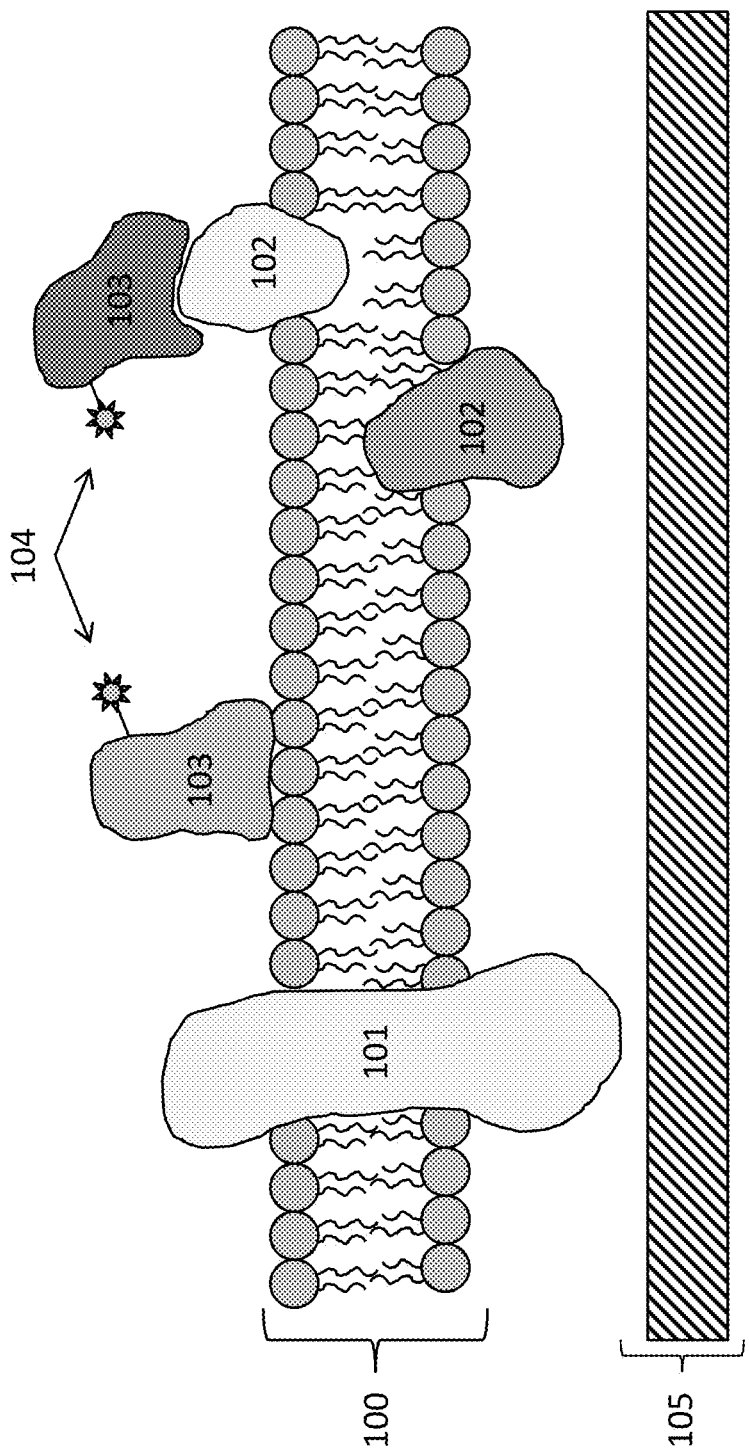
FIG. 3 provides a schematic illustration of the structure of a supported lipid bilayer, including the lipid bilayer, integral membrane proteins, peripheral membrane proteins, and the substrate that provides support. In some embodiments, peripheral membrane proteins may be labeled with one or more nonlinear-active labels. In some embodiments, integral membrane proteins or lipid molecules in the bilayer may optionally be labeled with one or more nonlinear-active labels that are the same or distinct from those attached to the peripheral membrane protein.

Referring to FIG. 3, peripheral membrane proteins (103) may bind to protein or lipid components of the lipid bilayer (100) which is in turn supported by the substrate (105) which comprises the optical interface. The interaction between one or more peripheral membrane proteins and membrane components may be covalent or non-covalent. The interaction between one or more peripheral membrane proteins and membrane components may be specific or non-specific. In some embodiments, the one or more peripheral membrane proteins (103) may interact with transmembrane proteins (101) or other integral membrane proteins (102). In some embodiments, the one or more peripheral membrane proteins (103) may interact directly with lipid components of the bilayer (100). In those embodiments where a peripheral membrane protein of interest interacts specifically with lipid components of the bilayer, it may be advantageous to adjust the lipid composition of the bilayer to enhance the degree of binding observed for the peripheral membrane protein, or to preserve the native functional state of the peripheral membrane protein. In many embodiments, the peripheral membrane protein (103) may be labeled with one or more nonlinear-active moieties (104), i.e. with one or more non-linear-active molecules, labels, or tags which may be the same or different. In some embodiments, other assay components, e.g. integral membrane components, lipid bilayer components, or other peripheral membrane proteins, may be labeled with one or more nonlinear-active moieties which may be the same or different. In many embodiments, the objective of the assay is to detect changes in binding interactions or conformational states of the one or more peripheral membrane proteins, or the components with which they interact, e.g. integral membrane proteins, as indicated by a change in the orientation or distance of the one or more nonlinear-active moieties relative to the plane of the substrate comprising the optical interface. In many embodiments, the objective of the assay is to detect changes in binding interactions or conformational states of the one or more peripheral membrane proteins, or the components with which they interact, upon exposure to or contact with one or more test entities or controls (e.g., known ligands).

As used herein, a control may be a positive control or a negative control. For example, a positive control may be a ligand that is known to bind to a peripheral membrane protein and induce a conformational change in the protein. Alternatively, a positive control may be a ligand that is known to bind to a peripheral membrane protein and block its interaction with a protein or lipid component of a biological membrane or supported lipid bilayer. A negative control may be a ligand that is known to bind to a peripheral membrane protein but not induce a conformational change or not block its interaction with a protein or lipid component of a biological membrane or supported lipid bilayer. In some embodiments, a negative control may comprise the addition of a buffer solution and the collection of a baseline or background signal. In some embodiments, the change in nonlinear optical signal, e.g. SHG intensity, for a labeled peripheral membrane protein may be monitored as a function of the concentration of a test entity with which it is contacted, and compared to that for the concentration of a positive or negative control. Those of skill in the art will recognize that there are a variety of controls that may be used in biological assays to aid in the interpretation of assay results.

In some embodiments, the disclosed methods, devices, and systems may be used to determine whether or not a candidate peripheral membrane protein (or mutant form thereof) is in fact and peripheral membrane protein by monitoring the binding interaction between the candidate peripheral membrane protein and a supported lipid bilayer. In some embodiments, the disclosed methods for identifying binding of a candidate peripheral membrane protein to a supported lipid bilayer may comprise: a) providing a substrate having a first substrate surface comprising a supported lipid bilayer, wherein the supported lipid bilayer comprises one or more lipid components and optionally one or more protein components; b) contacting the supported lipid bilayer with the candidate peripheral membrane protein, wherein the candidate peripheral membrane protein is labeled with a nonlinear-active label; c) illuminating the first substrate surface with excitation light of at least one fundamental frequency, wherein the excitation light is provided by at least one light source; and d) detecting light generated by the nonlinear-active label as a result of the illumination in step c) both before and after contacting the supported lipid bilayer with the candidate peripheral membrane protein, wherein a change in a physical property of the light detected before and after contacting the supported lipid bilayer with the candidate peripheral membrane protein is an indicator that the candidate peripheral membrane protein binds to the supported lipid bilayer or a component thereof. In some embodiments, the method may be performed using an artificial membrane, e.g., an artificial membrane supported on the substrate that comprises the optical interface, rather than a supported lipid bilayer, wherein the artificial membrane may be modified by attachment of one or more lipid, protein, membrane protein or other biomolecular components.

In some embodiments, the disclosed methods may be used for identifying a test agent that modulates a conformational state of a peripheral membrane protein, the methods comprising: a) providing a substrate having a first substrate surface comprising a supported lipid bilayer, wherein the supported lipid bilayer comprises one or more lipid components and optionally one or more protein components; b) contacting the supported lipid bilayer with the peripheral membrane protein, wherein the peripheral membrane protein binds to the supported lipid bilayer and is labeled with a first nonlinear-active label; c) illuminating the first substrate surface with excitation light of at least one fundamental frequency, wherein the excitation light is provided by at least one light source; and d) detecting light generated by the first nonlinear-active label as a result of the illumination in step c) both before and after contacting the bound peripheral membrane protein with the test agent, wherein a change in a physical property of the light detected upon contacting the peripheral membrane protein with the test agent is an indicator that the test agent modulates a change in the binding properties of the peripheral membrane protein to the membrane or the conformational state of the peripheral membrane protein. In some embodiments, the peripheral membrane protein is labeled with the first nonlinear-active label at a site that is known to undergo a local conformational change upon binding to a membrane component or upon binding of a known ligand. In some embodiments, the method may be performed using an artificial membrane, e.g., a substrate-supported artificial membrane, rather than a supported lipid bilayer, wherein the artificial membrane may be modified by attachment of one or more lipid, protein, membrane protein, or other biomolecular components.

In some embodiments, the peripheral membrane protein is labeled with a second nonlinear-active label attached to a site that does not undergo a conformational change to facilitate the ability to discriminate between ligand-induced conformational change and ligand-induced release from the supported lipid bilayer or artificial membrane. For example, when the peripheral membrane protein is labeled with a second nonlinear-active label attached to a site that does not undergo a conformational change, a change in a physical property of the detected light generated by the second nonlinear-active label by illumination with excitation light of an appropriate fundamental frequency and upon contact with the test agent may indicate that the conformational state of the peripheral membrane protein induced by the test agent results in release of the peripheral membrane protein from the supported lipid bilayer.

In some embodiments, the disclosed methods may be used for identifying a test agent that modulates binding of a peripheral membrane protein to a supported lipid bilayer. In these embodiments, the method may comprise: a) providing a substrate having a first substrate surface comprising a supported lipid bilayer, wherein the supported lipid bilayer comprises one or more lipid components and optionally one or more protein components; b) sequentially contacting the supported lipid bilayer with the peripheral membrane protein in the presence and in the absence of the test agent, wherein the peripheral membrane protein is labeled with a nonlinear-active label; c) illuminating the first substrate surface with excitation light of at least one fundamental frequency, wherein the excitation light is provided by at least one light source; and d) detecting light generated by the nonlinear-active label as a result of the illumination in step c) both in the presence and in the absence of the test agent, wherein a change in a physical property of the light detected in the presence and in the absence of the test agent is an indicator that the test agent modulates binding of the peripheral membrane protein to the supported lipid bilayer. In some embodiments, the method may be performed using an artificial membrane, e.g., a supported artificial membrane, rather than a supported lipid bilayer, wherein the artificial membrane may be modified by attachment of one or more lipid, protein, membrane protein, or other biomolecular components.

In some embodiments, the disclosed methods may be used for identifying an agent B that binds to an allosteric site on a peripheral membrane protein conformation. In these embodiments, the methods may comprise: a) contacting the peripheral membrane protein with an agent A that binds to an active site of the peripheral membrane protein or wherein agent A is naturally bound to the active site of the peripheral membrane protein when isolated, and wherein the peripheral membrane protein is attached to a supported lipid bilayer; b) contacting the peripheral membrane protein with the agent B, wherein the peripheral membrane protein is labeled with a nonlinear-active label having a net orientation at an interface, wherein a detectable signal is generated by the nonlinear-active label using a surface selective technique, and wherein the detectable signal indicates a conformational change in the structure of the peripheral membrane protein produced when the agent B binds to an allosteric site on the peripheral membrane protein; and c) measuring the presence or absence of the detectable signal after the peripheral membrane protein has been contacted with the agent B. In some embodiments, the peripheral membrane protein is labeled with the nonlinear-active label at a site that is known to undergo a local conformational change upon binding to a membrane component or upon binding of a known ligand. In some embodiments, the method may be performed using an artificial membrane, e.g., a substrate-supported artificial membrane, rather than a supported lipid bilayer, wherein the artificial membrane may be modified by attachment of one or more lipid, protein, membrane protein, or other biomolecular components.

In some embodiments of the disclosed methods, the method may comprise: a) contacting a supported lipid bilayer that includes one or more lipid components and optionally one or more protein components with a peripheral membrane protein, wherein the peripheral membrane protein and/or one or more other lipid or protein components of the bilayer are labeled with one or more nonlinear-active labels; b) contacting the peripheral membrane protein with one or more ligands that may bind to the peripheral membrane protein or are known to bind to it; c) optionally washing out the one or more ligands; d) contacting the peripheral membrane protein with a test agent; and e) detecting light generated by the one or more nonlinear-active labels upon illumination with light of at least one fundamental frequency both before and after contacting the peripheral membrane protein with the test agent, and optionally before and after washing out the one or more ligands, wherein a change in a physical property of the detected light that is generated by the one or more nonlinear-active labels indicates a change in an interaction between the peripheral membrane protein and the one or more lipid and/or protein components. In some embodiments, the peripheral membrane protein and/or one or more other lipid or protein components may be labeled with a nonlinear-active label at a site that is known to undergo a local conformational change upon binding of the peripheral membrane protein and/or other protein component to a membrane component or upon binding of a known ligand. In some embodiments, the method may be performed using an artificial membrane, e.g., a substrate-supported artificial membrane, rather than a supported lipid bilayer, wherein the artificial membrane may be modified by attachment of one or more lipid, protein, membrane protein, or other biomolecular components.

In any of the embodiments disclosed herein, the method may further comprise adjusting the relative percentages of two or more lipid components in the supported lipid bilayer to enhance the degree of binding of the peripheral membrane protein to the supported lipid bilayer.

In any of the embodiments disclosed herein, the one or more nonlinear active-labels may comprise a second harmonic-active, sum frequency-active, or difference frequency-active label, or any combination thereof.

In any of the embodiments disclosed herein, the physical property of the detected light that is monitored may be selected from the group consisting of intensity, wavelength, polarization, the time-course of the intensity, the time-course of the wavelength, the time-course of the polarization, or any combination thereof.

High Throughput Systems and Methods

Systems and methods are also disclosed herein for implementing high throughput analysis of conformation or conformational change in peripheral membrane protein assays, or other biological assays, based on the use of second harmonic generation or related nonlinear optical detection techniques. As used herein, "high throughput" is a relative term used in comparison to structural measurements performed using traditional techniques such as NMR or X-ray crystallography. As will be described in more detail below, the SHG-based methods and systems disclosed herein are capable of performing structural determinations at a rate that is at least an order-of-magnitude faster than these conventional techniques.

In one aspect, this disclosure provides a method for high throughput detection of conformation or conformational change in one or more peripheral membrane proteins, or other biological entities, the method comprising (i) labeling one or more target peripheral membrane proteins with a nonlinear-active label or tag, (ii) immobilizing the one or more labeled target peripheral membrane proteins at one or more discrete regions of a planar substrate surface, wherein the substrate surface further comprises an optical interface, (iii) sequentially exposing each discrete region to excitation light by changing the position of the substrate relative to an external light source, (iv) collecting a nonlinear optical signal emitted from each discrete region as it is exposed to excitation light, and (v) processing said nonlinear optical signal to determine an orientation, conformation, or conformational change of each of the one or more biological entities. In another aspect, the method further comprises (vi) contacting each of the one or more target peripheral membrane proteins with one or more test entities following the first exposure to excitation light, (vii) subsequently re-exposing each discrete region to excitation light one or more times, (viii) collecting a nonlinear optical signal from each discrete region as it is exposed to excitation light, and (ix) processing said nonlinear optical signals to determine whether or not a change in orientation or conformation has occurred in the one or more peripheral membrane proteins as a result of contacting with said one or more test entities. In one aspect of the method, nonlinear optical signals are detected only once following contact of the one or more target peripheral membrane proteins with one or more test entities (i.e. endpoint assay mode), and then used to determine whether or not conformational change has occurred. In another aspect, nonlinear optical signals are collected repeatedly and at defined time intervals following contact of the one of more target peripheral membrane proteins with one or more test entities (i.e. kinetics mode), and then used to determine the kinetics of conformational change in the one or more target peripheral membrane proteins. In a preferred aspect of the method, each discrete region of the substrate comprises a supported lipid bilayer structure, and peripheral membrane proteins are immobilized in each discrete region by means of binding to protein and/or lipid components of the lipid bilayer. In another preferred aspect of the method, the excitation light is delivered to the substrate surface, i.e. the optical interface, by means of total internal reflection, and the nonlinear optical signals emitted from the discrete regions of the substrate surface are collected along the same optical axis as the reflected excitation light.

In order to implement high throughput analysis of conformation or conformational change using nonlinear optical detection, the systems described herein require several components (illustrated schematically in FIG. 4), including (i) at least one suitable excitation light source and optics for delivering the at least one excitation light beam to an optical interface, (ii) an interchangeable substrate comprising the optical interface, to which one or more peripheral membrane proteins or other biological entities have been tethered or immobilized in discrete regions of the substrate, (iii) a high-precision translation stage for positioning the substrate relative to the at least one excitation light source, and (iv) optics for collecting nonlinear optical signals generated as a result of illuminating each of the discrete regions of the substrate with excitation light and delivering said nonlinear signals to a detector, and (v) a processor for analyzing the nonlinear optical signal data received from the detector and determining conformation or conformational change for the one or more biological entities immobilized on the substrate. In some aspects, the systems and methods disclosed herein further comprise the use of (vi) a programmable fluid-dispensing system for delivering test entities to each of the discrete regions of the substrate, and (vii) the use of plate-handling robotics for automated positioning and replacement of substrates at the interface with the optical system.

The methods and systems disclosed herein may be configured for analysis of a single peripheral membrane protein or biological entity contacted with a plurality of test entities, or for analysis of a plurality of peripheral membrane proteins or biological entities contacted with a single test entity, or any combination thereof. When contacting one or more biological entities with a plurality of test entities, the contacting step may be performed sequentially, i.e. by exposing the immobilized biological entity to a single test entity for a specified period of time, followed by an optional rinse step to remove the test entity solution and regenerate the immobilized biological entity prior to introducing to the next test entity, or the contacting step may be performed in parallel, i.e. by having a plurality of discrete regions comprising the same immobilized biological entity, and exposing the biological entity in each of the plurality of discrete regions to a different test entity. The methods and systems disclosed herein may be configured to perform analysis of conformational change in at least one biological entity, at least two biological entities, at least four biological entities, at least six biological entities, at least eight biological entities, at least ten biological entities, at least fifteen biological entities, or at least twenty biological entities. In some aspects, methods and systems disclosed herein may be configured to perform analysis of conformational change in at most twenty biological entities, at most fifteen biological entities, at most ten biological entities, at most eight biological entities, at most six biological entities, at most four biological entities, at most two biological entities, or at most one biological entity. Similarly, the methods and systems disclosed herein may be configured to perform analysis of conformational change upon exposure of the one or more biological entities to at least 1 test entity, at least 5 test entities, at least 10 test entities, at least 50 test entities, at least 100 test entities, at least 500 test entities, at least 1,000 test entities, at least 5,000 test entities, at least 10,000 test entities, or at least 100,000 test entities. In some aspects, the methods and systems disclosed herein may be configured to perform analysis of conformational change upon exposure of the one or more biological test entities to at most 100,000 test entities, at most 10,000 test entities, at most 5,000 test entities, at most 1,000 test entities, at most 500 test entities, at most 100 test entities, at most 50 test entities, at most 10 test entities, at most 5 test entities, or at most 1 test entity.

Biological Entities and Test Entities

As used herein, the phrase "biological entities" (or target molecules) comprises but is not limited to cells, proteins, peptides, receptors, enzymes, antibodies, DNA, RNA, biological molecules, oligonucleotides, solvents, small molecules, synthetic molecules, carbohydrates, or any combination thereof. In preferred embodiments of the present disclosure, the biological entities are peripheral membrane proteins. Examples of peripheral membrane proteins include, but are not limited to, phospholipases, cholesterol oxidases, glycosyltransferase, protein kinase C, spectrin, actin, glycolipid transfer proteins, sterol carrier proteins, phosphatidylinositol transfer proteins, cytochrome C, cupredoxins, adrenodoxin reductase, some flavoproteins, venoms, toxins, annexin, synapsin I, synuclein, blood coagulation factors and components, subunits or subdomains thereof, and any combination thereof.

Similarly, the phrase "test entities" (or test agents) also comprises but is not limited to cells, proteins, peptides, receptors, enzymes, antibodies, DNA, RNA, biological molecules, oligonucleotides, solvents, small molecules, synthetic molecules, carbohydrates, or any combination thereof. In some embodiments of the present disclosure, the test entities may be other peripheral membrane proteins, integral membrane proteins, or subunits or subdomains thereof.

In some aspects, peripheral membrane proteins or other biological entities may comprise drug targets, or portions thereof, while test entities may comprise drug candidates, or portions thereof.

Nonlinear-Active Labels and Labeling Techniques

As noted above, most biological molecules are not intrinsically nonlinear-active. Exceptions include collagen, a structural protein that is found in most structural or load-bearing tissues. SHG microscopy has been used extensively in studies of collagen-containing structures, for example, the cornea. Other biological molecules or entities must be rendered nonlinear-active by means of introducing a non-linear-active labels allows a direct optical means of detecting interactions between the labeled biological molecule or entity and another molecule or entity (i.e. the test entity) in cases where the interaction results in a change in orientation or conformation of the biological molecule or entity using a surface-selective nonlinear optical technique.

In alternative aspects of the methods and systems described herein, at least two distinguishable nonlinear-active labels are used. The orientation of the attached two or more distinguishable labels would then be chosen to facilitate well defined directions of the emanating coherent nonlinear light beam. The two or more distinguishable labels can be used in assays where multiple fundamental light beams at one or more frequencies, incident with one or more polarization directions relative to the optical interface are used, with the resulting emanation of at least two nonlinear light beams.

Examples of nonlinear-active tags or labels include, but are not limited to, the compounds listed in Table 1, and their derivatives.

TABLE 1

| Examples of Nonlinear-Active Tags | | |
|---|---|---|
| 2-aryl-5-(4-pyridyl)oxazole | Fluoresceins | Polyenes |
| 2-(4-pyridyl)-cycloalkano[d]oxazoles | Hemicyanines | Polyimides |
| 5-aryl-2-(4-pyridyl)oxazole | Indandione-1,3-pyidinium betaine | Polymethacrylates |
| 7-Hydroxycoumarin-3-carboxylic acid, succinimidyl ester | Indodicarbocyanines | PyMPO (pyridyloxazole) |
| Azo dyes | Melamines | PyMPO, succinimidyl ester (1-(3-(succinimidyloxycarbonyl)benzyl)-4-(5-(4-methoxyphenyl)oxazol-2-yl)pyridinium bromide) PyMPO, maleimide (1-(2-maleimidylethyl)-4-(5-(4-methoxyphenyl) oxazol-2-yl)pyridinium methanesulfonate) |
| 6-bromoacetyl-2-dimethylaminonaphthalene (Badan) | Merocyanines | Stilbazims |
| Benzooxazoles | Methoxyphenyl)oxazol-2-yl)pyridinium bromide) | Stilbenes |
| Bithiophenes | Methylene blue | Stryryl-based dyes |
| Cyanines | Oxazole or oxadizole molecules | Sulphonyl-substituted azobenzenes |
| Dapoxyl carboxylic acid, succinimidyl ester | Oxonols | Thiophenes |
| Diaminobenzene compounds | Perylenes | Tricyanovinyl aniline |
| Diazostilbenes | Phenothiazine-stilbazole | Tricyanovinyl azo | linear-active moiety such as a tag or label. A label for use in the present invention refers to a nonlinear-active moiety, tag, molecule, or particle which can be bound, either covalently or non-covalently to a molecule, particle or phase (e.g., a lipid bilayer) in order to render the resulting system more nonlinear optical active. Labels can be employed in the case where the molecule, particle or phase (e.g., lipid bilayer) is not nonlinear active to render the system nonlinear-active, or with a system that is already nonlinear-active to add an extra characterization parameter into the system. Exogenous labels can be pre-attached to the molecules, particles, or other biological entities, and any unbound or unreacted labels separated from the labeled entities before use in the methods described herein. In a specific aspect of the methods disclosed herein, the nonlinear-active moiety is attached to the target molecule or biological entity in vitro prior to immobilizing the target molecules or biological entities in discrete regions of the substrate surface. The labeling of biological molecules or other biological entities with non- In evaluating whether a species may be nonlinear-active, the following characteristics can indicate the potential for nonlinear activity: a large difference dipole moment (difference in dipole moment between the ground and excited states of the molecule), a large Stokes shift in fluorescence, or an aromatic or conjugated bonding character. In further evaluating such a species, an experimenter can use a simple technique known to those skilled in the art to confirm the nonlinear activity, for example, through detection of SHG from an air-water interface on which the nonlinear-active species has been distributed. Once a suitable nonlinear-active species has been selected for the experiment at hand, the species can be conjugated, if desired, to a biological molecule or entity for use in the surface-selective nonlinear optical methods and systems disclosed herein.

The following reference and references therein describe techniques available for creating a labeled biological entity from a synthetic dye and many other molecules: Greg T. Hermanson, Bioconjugate Techniques, Academic Press, New York, 1996.

In a specific aspect of the methods and systems disclosed, metal nanoparticles and assemblies thereof are modified to create biological nonlinear-active labels. The following references describe the modification of metal nanoparticles and assemblies: J. P. Novak and D. L. Feldheim, "Assembly of Phenylacetylene-Bridged Silver and Gold Nanoparticle Arrays", J. Am. Chem. Soc. 122:3979-3980 (2000); J. P. Novak, et al., "Nonlinear Optical Properties of Molecularly Bridged Gold Nanoparticle Arrays", J. Am. Chem. Soc. 122:12029-12030 (2000); Vance, F. W., Lemon, B. I., and Hupp, J. T., "Enormous Hyper-Rayleigh Scattering from Nanocrystalline Gold Particle Suspensions", J. Phys. Chem. B 102:10091-93 (1999).

In some embodiments, one or more nonlinear-active labels may be attached to one or more different positions within the same peripheral membrane protein or other lipid or protein component of the assay system. In some embodiments, the one or more nonlinear-active labels may be attached to one or more different positions (e.g. sites) in different molecules of the same protein, i.e., to create a family of proteins comprising different versions of the labeled protein. In some embodiments, the number of labeling sites at which the protein (or family of proteins) is labeled may be at least 1 site, at least 2 sites, at least 3 sites, at least 4 sites, at least 5 sites, at least 6 sites, at least 7 sites, at least 8 sites, at least 9 sites, at least 10 sites, or more. In other embodiments, the nonlinear-active label may be attached to different single-site cysteine mutants or variants of the same protein, or nonlinear-active unnatural amino acids (e.g., Aladan or other naphthalene derivatives) may be incorporated into a family of mutants or variants at one or more sites. Such proteins can be engineered, naturally occurring, made using in vitro translation methods, expressed in vivo, and in general created through any of the various methods known to those skilled in the art.

In some embodiments, the nonlinear optical measurements of the disclosed methods, e.g., SHG measurements, may comprise using protein molecules (or other biological molecules) labeled with a single nonlinear-active label. In some embodiments, the SHG measurements may comprise using protein molecules labeled with at least 2 different nonlinear-active labels, at least 3 different nonlinear-active labels, at least 4 different nonlinear-active labels, at least 5 different nonlinear-active labels, at least 6 different nonlinear-active labels, at least 7 different nonlinear-active labels, at least 8 different nonlinear-active labels, at least 9 different nonlinear-active labels, or at least 10 different nonlinear-active labels.

In preferred embodiments, genetic engineering techniques may be used to incorporate nonlinear-active unnatural amino acids (e.g., Aladan or other naphthalene derivatives) at one or more specific sites within the biological molecule, e.g., a protein molecule, using any of a variety of techniques known to those of skill in the art. See, for example, Cohen, et al. (2002), "Probing Protein Electrostatics with a Synthetic Fuorescence Amino Acid", Science 296:1700-1703, and U.S. Pat. No. 9,182,406.

Types of Biological Interactions Detected

The methods and systems disclosed herein provide for detection of a variety of interactions between biological entities, e.g., between peripheral membrane proteins and membrane proteins or lipids, or between peripheral membrane proteins and test entities, depending on the choice of biological entities, test entities, and non-linear active labeling technique employed. In one aspect, the present disclosure provides for the qualitative detection of binding events, e.g. the binding of a ligand to a peripheral membrane protein, as indicated by the resulting conformational change induced in the peripheral membrane protein. In another aspect, the present disclosure provides for quantitative analysis of binding or activation events, e.g. the binding of a ligand to a peripheral membrane protein that triggers a conformational change, by performing replicate measurements using different concentrations of the ligand molecule and generating a dose-response curve using the percent change in maximal conformational change observed. Similarly, other aspects of the present disclosure may provide methods for qualitative or quantitative measurements of peripheral membrane protein—peripheral membrane protein interactions, peripheral-membrane protein—integral membrane protein interactions, peripheral membrane protein—phospholipid bilayer interactions, enzyme-inhibitor interactions, antibody-antigen interactions, the formation of complexes of biological macromolecules, or interactions of receptors with allosteric modulators.

Interactions between biological entities or biological and test entities (e.g. binding reactions, conformational changes, etc.) can be correlated through the methods presently disclosed to the following measurable nonlinear signal parameters: (i) the intensity of the nonlinear light, (ii) the wavelength or spectrum of the nonlinear light, (iii) the polarization of the nonlinear light, (iv) the time-course of (i), (ii), or (iii), and/or vi) one or more combinations of (i), (ii), (iii), and (iv).

Laser Light Sources and Excitation Optical System

Figure 5:
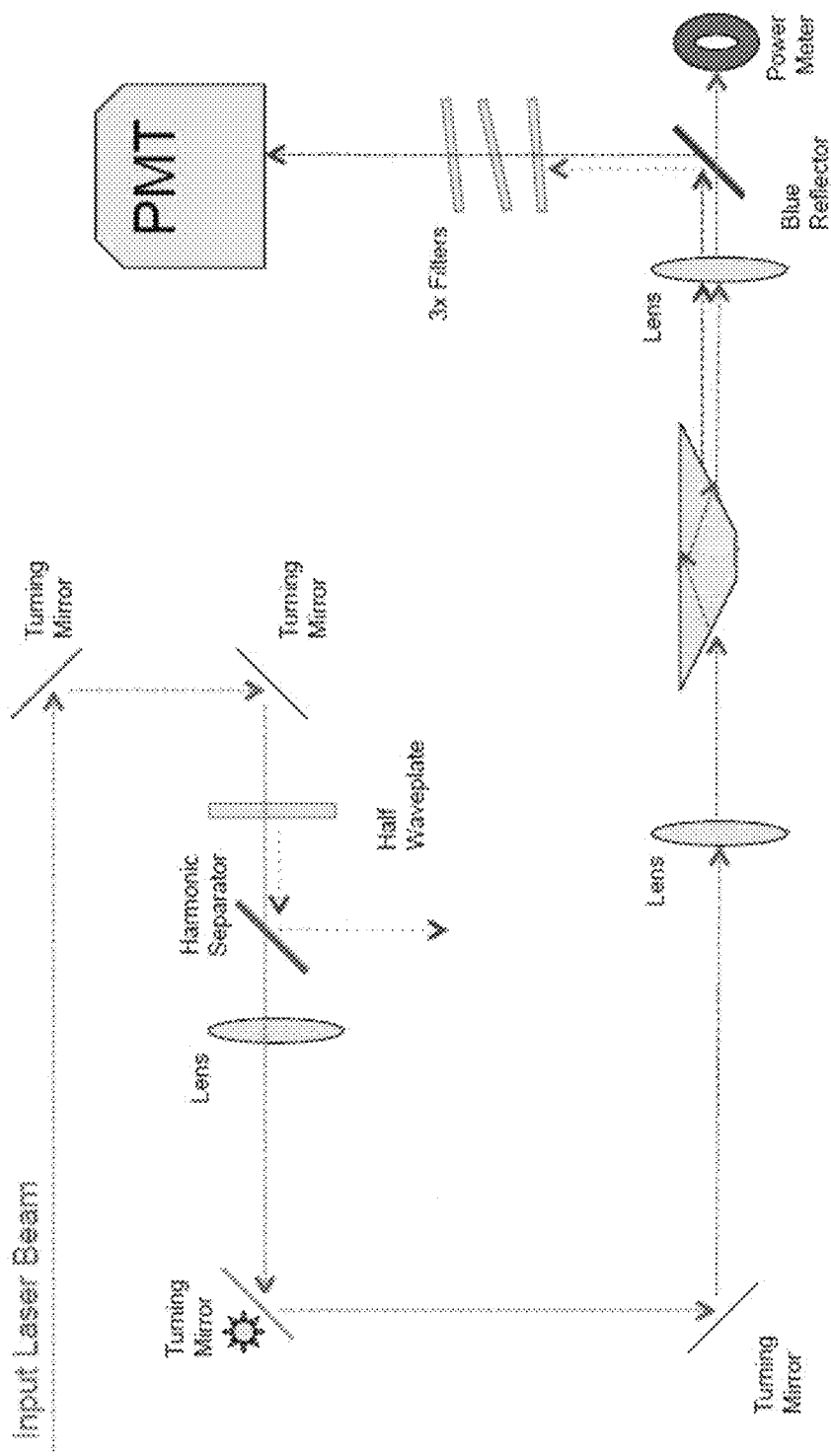
FIG. 5 shows a schematic for one non-limiting example of an optical setup used for analysis of conformational change in biological molecules using nonlinear optical detection.

FIG. 5 illustrates one aspect of the methods and systems disclosed herein wherein second harmonic light is generated by reflecting incident fundamental excitation light from the surface of a substrate (FIG. 6) comprising the sample interface (or optical interface). A laser provides the fundamental light necessary to generate second harmonic light at the sample interface. Typically this will be a picosecond or femtosecond laser, either wavelength tunable or not tunable, and commercially available (e.g. a Ti:Sapphire femtosecond laser or fiber laser system). Light at the fundamental frequency (w) exits the laser and its polarization is selected using, for example a half-wave plate appropriate to the frequency and intensity of the light (e.g., available from Melles Griot, Oriel, or Newport Corp.). The beam then passes through a harmonic separator designed to pass the fundamental light but block nonlinear light (e.g. second harmonic light). This filter is used to prevent back-reflection of the second harmonic beam into the laser cavity which can cause disturbances in the lasing properties. A combination of mirrors and lenses are then used to steer and shape the beam prior to reflection from a final mirror that directs the beam via a prism to impinge at a specific location and with a specific angle θ on the substrate surface such that it undergoes total internal reflection at the substrate surface. One of the mirrors in the optical path can be scanned if required using a galvanometer-controlled mirror scanner, a rotating polygonal mirror scanner, a Bragg diffractor, acousto-optic deflector, or other means known in the art to allow control of a mirror's position. The substrate comprising the optical interface and nonlinear-active sample surface can be mounted on an x-y translation stage (computer controlled) to select a specific location on the substrate surface for generation of the second harmonic beam. In some aspects of the methods and systems presently described, it is desirable to scan or rotate one mirror in order to slightly vary the angle of incidence for total internal reflection, and thereby maximize the nonlinear optical signal emitted from the discrete regions of the substrate surface without substantially changing the position of the illuminating excitation light spot. In some aspects, two (or more) lasers having different fundamental frequencies may be used to generate sum frequency or difference frequency light at the optical interface on which the non-linear active sample is immobilized.

Substrate Formats, Optical Interface, and Total Internal Reflection

As described above, the systems and methods of the present disclosure utilize a planar substrate for immobilization of one or more peripheral membrane proteins, or other biological entities, on a top surface of the substrate, wherein the top substrate surface further comprises the optical interface (or sample interface) used for exciting nonlinear optical signals. The substrate can be glass, silica, fused-silica, plastic, or any other solid material that is transparent to the fundamental and second harmonic light beams, and that supports total internal reflection at the substrate/sample interface when the excitation light is incident at an appropriate angle. In some aspects of the invention, the discrete regions within which biological entities are contained are configured as one-dimensional or two-dimensional arrays, and are separated from one another by means of a hydrophobic coating or thin metal layer. In other aspects, the discrete regions may comprise indents in the substrate surface. In still other aspects, the discrete regions may be separated from each other by means of a well-forming component such that the substrate forms the bottom of a microwell plate (or microplate), and each individual discrete region forms the bottom of one well in the microwell plate. In one aspect of the present disclosure, the well-forming component separates the top surface of the substrate into 96 separate wells. In another aspect, the well-forming component separates the top surface of the substrate into 384 wells. In yet another aspect, the well-forming component separates the top surface of the substrate into 1,536 wells. In all of these aspects, the substrate, whether configured in a planar array, indented array, or microwell plate format, may comprise a disposable or consumable device or cartridge that interfaces with other optical and mechanical components of the high throughput system.

The methods and systems disclosed herein further comprise specifying the number of discrete regions or wells into which the substrate surface is divided, irrespective of how separation is maintained between discrete regions or wells. Having larger numbers of discrete regions or wells on a substrate may be advantageous in terms of increasing the sample analysis throughput of the method or system. In one aspect of the present disclosure, the number of discrete regions or wells per substrate is between 10 and 1,600. In other aspects, the number of discrete regions or wells is at least 10, at least 20, at least 50, at least 100, at least 200, at least 300, at least 400, at least 500, at least 750, at least 1,000, at least 1,250, at least 1,500, or at least 1,600. In yet other aspects of the disclosed methods and systems, the number of discrete regions or wells is at most 1,600, at most 1,500, at most 1,000, at most 750, at most 500, at most 400, at most 300, at most 200, at most 100, at most 50, at most 20, or at most 10. In a preferred aspect, the number of discrete regions or wells is 96. In another preferred aspect, the number of discrete regions or wells is 384. In yet another preferred aspect, the number of discrete regions or wells is 1,536. Those of skill in the art will appreciate that the number of discrete regions or wells may fall within any range bounded by any of these values (e.g. from about 12 to about 1,400).

The methods and systems disclosed herein also comprise specifying the surface area of the discrete regions or wells into which the substrate surface is divided, irrespective of how separation is maintained between discrete regions or wells. Having discrete regions or wells of larger area may facilitate ease-of-access and manipulation of the associated biological entities in some cases, whereas having discrete regions or wells of smaller area may be advantageous in terms of reducing assay reagent volume requirements and increasing the sample analysis throughput of the method or system. In one aspect of the present disclosure, the surface area of the discrete regions or wells is between 1 $mm^2$ and 100 $mm^2$. In other aspects, the area of the discrete regions or wells is at least 1 $mm^2$, at least 2.5 $mm^2$, at least 5 $mm^2$, at least 10 $mm^2$, at least 20 $mm^2$, at least 30 $mm^2$, at least 40 $mm^2$, at least 50 $mm^2$, at least 75 $mm^2$, or at least 100 $mm^2$. In yet other aspects of the disclosed methods and systems, the area of the discrete regions or wells is at most 100 $mm^2$, at most 75 $mm^2$, at most 50 $mm^2$, at most 40 $mm^2$, at most 30 $mm^2$, at most 20 $mm^2$, at most 10 $mm^2$, at most 5 $mm^2$, at most 2.5 $mm^2$, or at most 1 $mm^2$. In a preferred aspect, the area of discrete regions or wells is about 35 $mm^2$. In another preferred aspect, the area of the discrete regions or wells is about 8.6 $mm^2$. Those of skill in the art will appreciate that the area of the discrete regions or wells may fall within any range bounded by any of these values (e.g. from about 2 $mm^2$ to about 95 $mm^2$).

Discrete regions of the substrate surface are sequentially exposed to (illuminated with) excitation light by re-positioning the substrate relative to the excitation light source. Total internal reflection of the incident excitation light creates an "evanescent wave" at the sample interface which excites the nonlinear-active label and results in generation of second harmonic light (or in some aspects, sum frequency or difference frequency light). Because the intensity of the evanescent wave, and hence the intensity of the nonlinear optical signals generated, is dependent on the incident angle of the excitation light beam, precise orientation of the substrate plane with respect to the optical axis of the excitation beam and efficient optical coupling of the beam to the substrate is critical for achieving optimal SHG signal across the array of discrete regions. In some aspects of the present disclosure, total internal reflection is achieved by means of a single reflection of the excitation light from the substrate surface. In other aspects, the substrate may be configured as a waveguide such that the excitation light undergoes multiple total internal reflections as it propagates along the waveguide. In yet other aspects, the substrate may be configured as a zero-mode waveguide, wherein an evanescent field is created by means of nanofabricated structures.

Figure 6:
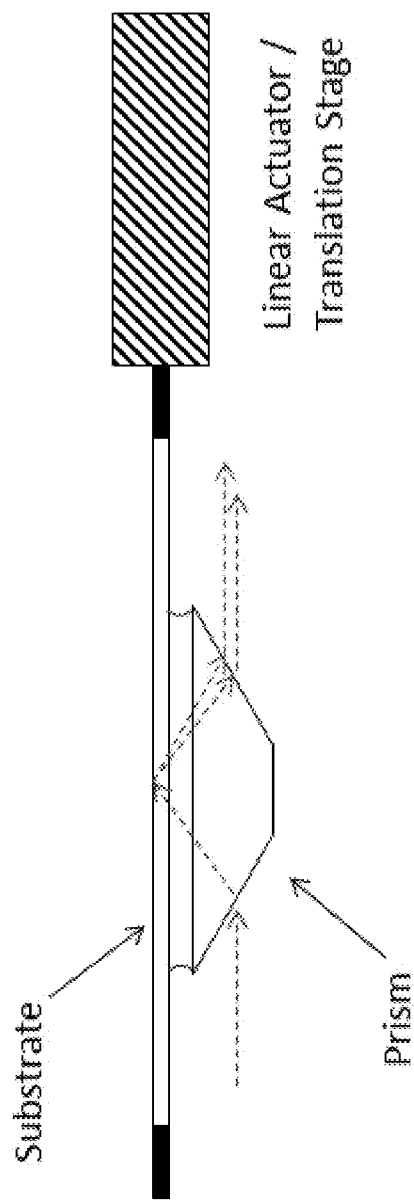
FIG. 6 shows a schematic illustration depicting the use of a prism to direct excitation light at an appropriate incident angle such that the excitation light undergoes total internal reflection at the top surface of a substrate. The two dashed lines to the right of the prism indicate the optical path of the reflected excitation light and the nonlinear optical signal generated at the substrate surface when nonlinear-active species are tethered to the surface. The substrate is optionally connected to the actuator of an X-Y translation stage for re-positioning between measurements. The curved lines between the top surface of the prism and the lower surface of the substrate indicate the presence a thin layer (not to scale) of index-matching fluid used to ensure high optical coupling efficiency between the prism and substrate.

Efficient optical coupling between the excitation light beam and the substrate in an optical setup such as the one illustrated in FIGS. 5 and 6 would typically be achieved by use of an index-matching fluid such as mineral oil, mixtures of mineral oil and hydrogenated terphenyls, perfluorocarbon fluids, glycerin, glycerol, or similar fluids having a refractive index near 1.5, wherein the index-matching fluid is wicked between the prism and the lower surface of the substrate. Since a static, bubble-free film of index-matching fluid is likely to be disrupted during fast re-positioning of the substrate, the systems and methods disclosed herein include alternative approaches for creating efficient optical coupling of the excitation beam to the substrate in high throughput systems.

FIGS. 7A-C illustrate one aspect of a high throughput system of the present disclosure in which a continuously recirculating stream of index-matching fluid is used to maintain efficient optical coupling between the prism, which is mounted as part of the optical system, and the substrate, which is configured in a microwell plate format (e.g. a glass bottom microplate format) and is free to translate relative to the prism. The continuous flow of index-matching fluid in this case ensures that the thin film of fluid between the prism and substrate is never disrupted as the two components move relative to each other, i.e. any small bubbles or discontinuities in the thin layer of fluid will be eliminated or pushed out from the gap between the prism and substrate by means of the fluid flow. Index-matching fluid is introduced into the gap via the two fluid channels indicated in the drawing, and may be collected in a suitable reservoir or sump, from which it may be recirculated using a small pump. In an alternative implementation of the same concept, instead of the line-contact between substrate and prism indicated in FIG. 7B, point contact between a single discrete region and a cylindrical total internal reflection (TIR) probe would be utilized, where the index-matching fluid would flow up through a center fluid channel, and then down over the sides of the cylindrical TIR probe to be collected in a suitable reservoir or sump.

Figure 8:
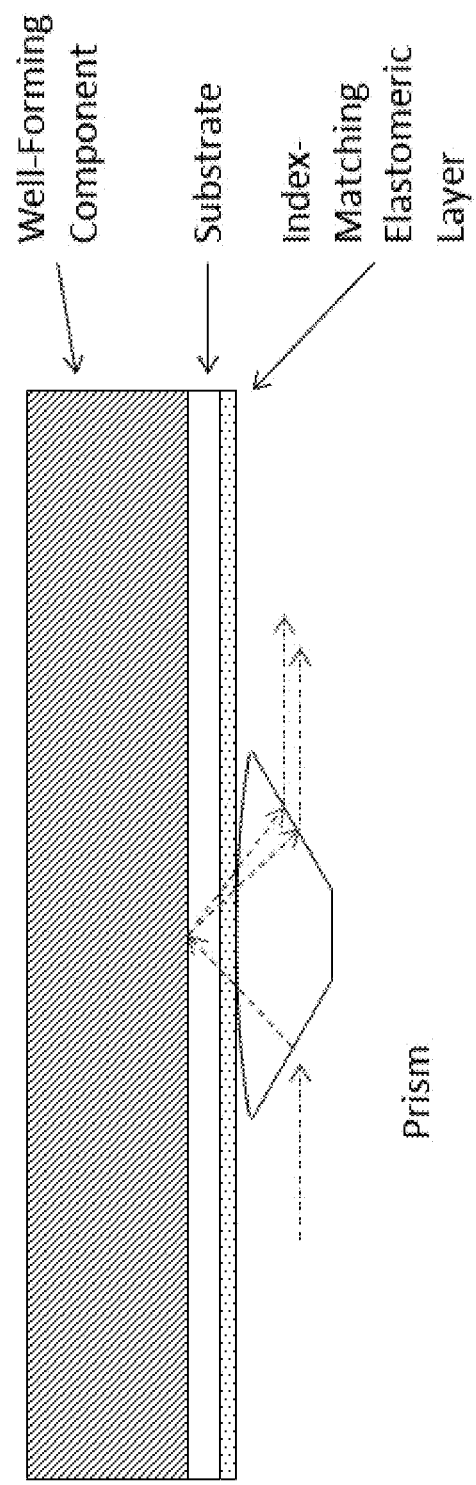
FIG. 8 shows a schematic illustration depicting the use of a layer of index-matching elastomeric material attached or adjacent to the lower surface of a transparent substrate (configured in a microwell plate format in this example) to ensure high optical coupling efficiency between a prism and the upper surface of the substrate. In some embodiments of this approach, the upper surface of the prism is slightly domed to focus the compression force when bringing the microwell plate and prism into contact, thereby reducing or eliminating the formation of air gaps between the prism and elastomeric material.

FIG. 8 illustrates another aspect of a high throughput system of the present disclosure, in which a thin layer of index-matching elastomeric material is used in place of index-matching fluid to maintain efficient optical coupling between the prism and substrate. In this case, the substrate is again packaged in a microwell plate format (e.g. a glass bottom microplate format), but with a thin layer of an index-matching elastomeric material attached to or adjacent to the lower surface of the substrate, such that when placed in contact with the upper surface of the prism, the elastomer fills the gap between prism and substrate and provides for efficient optical coupling. Examples of elastomeric materials that may be used include, but are not limited to silicones having a refractive index of about 1.4. In one aspect of the present disclosure, the refractive index of the elastomeric material is between about 1.35 and about 1.6. In other aspects, the index of refraction is about 1.6 or less, about 1.55 or less, about 1.5 or less, about 1.45 or less, about 1.4 or less, or about 1.35 or less. In yet other aspects, the index of refraction is at least about 1.35, at least about 1.4, at least about 1.45, at least about 1.5, at least about 1.55, or at least about 1.6. Those of skill in the art will appreciate that the index of refraction of the elastomeric layer may fall within any range bounded by any of these values (e.g. from about 1.4 to about 1.6). In one aspect of this approach, the thickness of the layer of elastomeric material is between about 0.1 mm and 2 mm. In other aspects, the thickness of the elastomeric layer is at least 0.1 mm, at least 0.2 mm, at least 0.4 mm, at least 0.6 mm, at least 0.8 mm, at least 1.0 mm, at least 1.2 mm, at least 1.4 mm, at least 1.6 mm, at least 1.8 mm, or at least 2.0 mm. In another aspect of this approach, the thickness of the elastomeric layer is at most 2.0 mm, at most 1.8 mm, at most 1.6 mm, at most 1.4 mm, at most 1.2 mm, at most 1.0 mm, at most 0.8 mm, at most 0.6 mm, at most 0.4 mm, at most 0.2 mm, or at most 0.1 mm. Those of skill in the art will appreciate that the thickness of the elastomeric layer my fall within any range bounded by any of these values (e.g. from about 0.1 mm to about 1.5 mm). In another aspect of this approach, the upper surface of the prism has a partially-cylindrical ridge or is domed (FIG. 9) to focus the compression force and provide better contact between substrate, elastomeric layer, and prism surface. This approach may also require the use of a third axis of translation for positioning of the substrate, i.e. between excitation and detection steps, the substrate (microwell plate) would be raised slightly to eliminate contact between the elastomeric layer and the prism prior to re-positioning the substrate to the location of the next discrete region to be analyzed.

Figure 11:
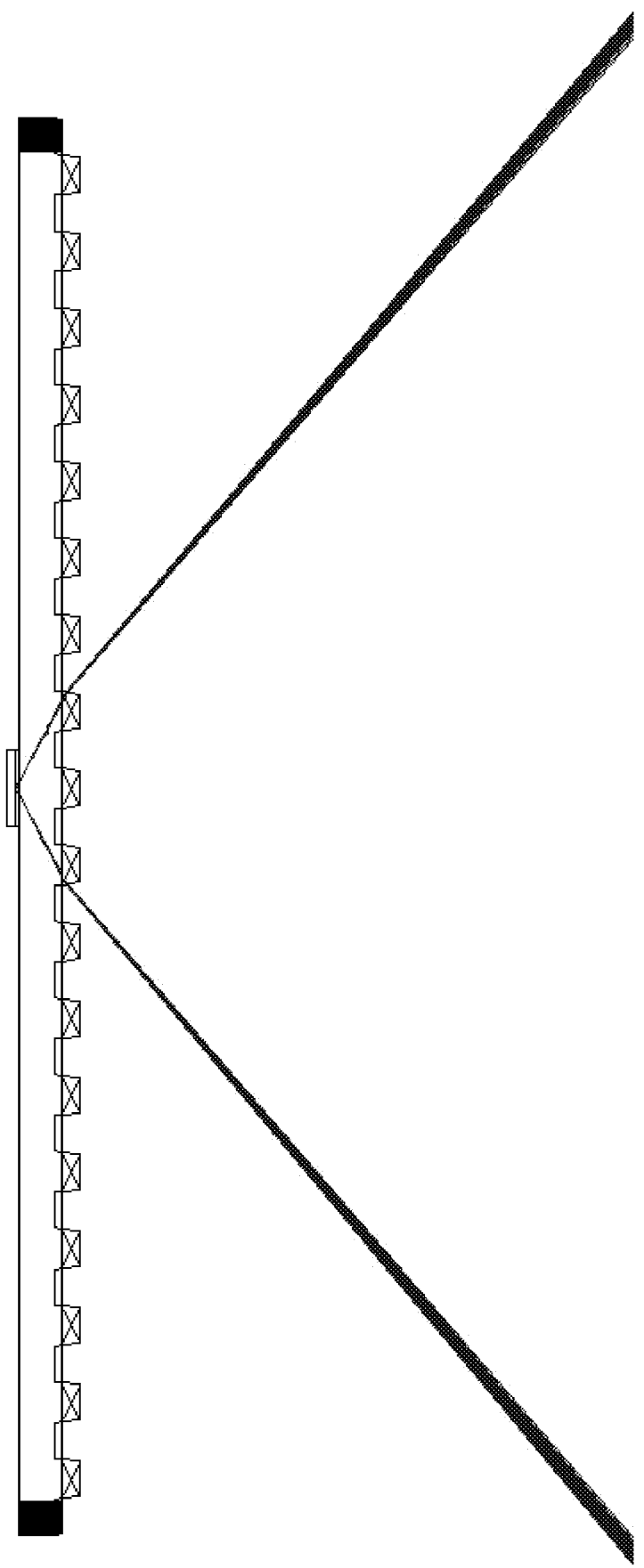
FIG. 11 illustrates the incident and exit light paths for coupling the excitation light to the substrate surface via total internal reflection using the design concept illustrated in FIGS. 9A-B.

FIGS. 9A-B and FIGS. 10A-B illustrate a preferred aspect of a high throughput system of the present disclosure, in which an array of prisms or gratings is integrated with the lower surface of the substrate (packaged in a microwell plate format) and used to replace the fixed prism, thereby eliminating the need for index-matching fluids or elastomeric layers entirely. The array of prisms (or gratings) is aligned with the array of discrete regions or wells on the upper surface of the substrate in such a way that incident excitation light is directed by an "entrance prism" ("entrance grating") to a discrete region or well that is adjacent to but not directly above the entrance prism (entrance grating), at an angle of incidence that enables total internal reflection of the excitation light beam from the sample interface (see FIG. 11), and such that the reflected excitation beam, and nonlinear-optical signals generated at the illuminated discrete region, are collected by an "exit prism" ("exit grating") that is again offset from (adjacent to but not directly underneath) the discrete region under interrogation, and wherein the entrance prism and exit prism (entrance grating and exit grating) for each discrete region are different, non-unique elements of the array.

In general, for an array of discrete regions comprising M rows×N columns of individual features, the corresponding prism or grating array will have M+2 rows×N columns or N+2 columns×M rows of individual prisms or gratings. In some embodiments, M may have a value of at least 2, at least 4, at least 6, at least 8, at least 12, at least 14, at least 16, at least 18, at least 20, at least 25, at least 30, at least 35, at least 40, at least 45, or at least 50 rows. In some embodiments, M may have a value of at most 50, at most 45, at most 40, at most 35, at most 30, at most 25, at most 20, at most 18, at most 16, at most 14, at most 12, at most 10, at most 8, at most 6, at most 4, or at most 2 rows. Similarly, in some embodiments, N may have a value of at least 2, at least 4, at least 6, at least 8, at least 12, at least 14, at least 16, at least 18, at least 20, at least 25, at least 30, at least 35, at least 40, at least 45, or at least 50 columns. In some embodiments, N may have a value of at most 50, at most 45, at most 40, at most 35, at most 30, at most 25, at most 20, at most 18, at most 16, at most 14, at most 12, at most 10, at most 8, at most 6, at most 4, or at most 2 columns. As will be apparent to those of skill in the art, M and N may have the same value or different values, and may have any value within the range specified above, for example, M=15 and N=45.

The geometry and dimensions of the individual prisms or gratings, including the thickness of the prism or grating array layer, are optimized to ensure that incident light undergoes total internal reflection at the selected discrete region of the substrate, and nonlinear optical signals generated at the selected discrete region are collected, with high optical coupling efficiency, independently of the position of substrate (microwell plate) relative to the excitation light beam. The prism or grating arrays may be fabricated by a variety of techniques known to those of skill in the art, for example, in a preferred aspect, they may be injection molded from smooth flowing, low birefringence materials such as cyclic olefin copolymer (COC) or cyclic olefin polymer (COP), acrylic, polyester, or similar polymers. In some aspects, the prism or grating array may be fabricated as a separate component, and subsequently integrated with the lower surface of the substrate. In other aspects, the prism or grating array may be fabricated as an integral feature of substrate itself.

Immobilization Chemistries

As disclosed herein, substrates in any of the formats described above are further configured for immobilization (also referred to as tethering or attachment) of biological entities within the specified discrete regions. Immobilization of biological molecules or cells may be accomplished by a variety of techniques known to those of skill in the art, for example, through the use of aminopropyl silane chemistries to functionalize glass or fused-silica surfaces with amine functional groups, followed by covalent coupling using amine-reactive conjugation chemistries, either directly with the biological molecule of interest, or via an intermediate spacer or linker molecule. Non-specific adsorption may also be used directly or indirectly, e.g. through the use of BSA-NHS(BSA-N-hydroxysuccinimide) by first attaching a molecular layer of BSA to the surface and then activating it with N,N'-disuccinimidyl carbonate. The activated lysine, aspartate or glutamate residues on the BSA react with surface amines on proteins.

In a preferred aspect of the present disclosure, biological molecules including integral membrane proteins may be immobilized on the surface by means of tethering to or embedding in "supported lipid bilayers", the latter comprising small patches of lipid bilayer confined to a silicon or glass surface by means of hydrophobic and electrostatic interactions, where the bilayer is "floating" above the substrate surface on a thin layer of aqueous buffer. Supported phospholipid bilayers can also be prepared with or without membrane proteins or other membrane-associated components as described, for example, in Salafsky et al., "Architecture and Function of Membrane Proteins in Planar Supported Bilayers: A Study with Photosynthetic Reaction Centers", Biochemistry 35 (47): 14773-14781 (1996); Gennis, R., *Biomembranes*, Springer-Verlag, 1989; Kalb et al., "Formation of Supported Planar Bilayers by Fusion of Vesicles to Supported Phospholipid Monolayers", Biochimica Biophysica Acta. 1103:307-316 (1992); and Brian et al. "Allogeneic Stimulation of Cytotoxic T-cells by Supported Planar Membranes", PNAS-Biological Sciences 81(19): 6159-6163 (1984), relevant portions of which are incorporated herein by reference. Supported phospholipid bilayers are well known in the art and there are numerous techniques available for their fabrication. Supported bilayers should typically be submerged in aqueous solution to prevent their destruction when exposed to air.

In some embodiments of the disclosed methods and devices, it may be advantageous to vary the lipid composition of the supported lipid bilayer, e.g. the number of different lipid components and/or their relative concentrations, in order to improve binding of peripheral membrane proteins, preserve the native structure of peripheral membrane proteins, and/or to mimic the physiological responses observed in vivo. Examples of lipid molecules that may be used to form supported lipid bilayers or that may be inserted as major or minor components of the supported lipid bilayer include, but are not limited to, diacylglycerol, phosphatidic acid (PA), phosphatidylethanolamine (PE), phosphatidylcholine (PC), phosphatidylserine (PS), phosphatidylinositol (PI), phosphatidylinositol phosphate (PIP), phosphatidylinositol biphosphate (PIP2), phosphatidylinositol triphosphate (PIP3), ceramide phosphorylcholine (sphingomyelin; SPH), ceramide phosphorylethanolamine (sphingomyelin; Cer-PE), ceramide phosphoryllipid, cholesterol, or any combination thereof.

In some embodiments the number of different lipid components of the supported lipid bilayer may range from 1 to 10, or more. In some embodiments, the number of different lipid components may be at least 1, at least 2, at least 3, at least 4, at least 5, at least 6, at least 7, at least 8, at least 9, or at least 10. In some embodiments, the number of different lipid components may be at most 10, at most 9, at most 8, at most 7, at most 6, at most 5, at most 4, at most 3, at most 2, or at most 1.

In some embodiments, the relative percentage of a given lipid component of the supported lipid bilayer may range from about 0.1% to about 100%. In some embodiments, the relative percentage of a given lipid component may be at least about 0.1%, at least about 0.2%, at least about 0.3%, at least about 0.4%, at least about 0.5%, at least about 1%, at least about 5%, at least about 10%, at least about 20%, at least about 30%, at least about 40%, at least about 50%, at least about 60%, at least about 70%, at least about 80%, at least about 90%, or at least about 100%. In some embodiments, the relative percentage of a given lipid component may be at most about 100%, at most about 90%, at most about 80%, at most about 70%, at most about 60%, at most about 50%, at most about 40%, at most about 30%, at most about 20%, at most about 10%, at most about 5%, at most about 1%, at most about 0.5%, at most about 0.4%, at most about 0.3%, at most about 0.2%, or at most about 0.1%. Those of skill in the art will recognize that the relative percentage of a given lipid component in the supported lipid bilayer may have any value within this range, e.g. about 12.5%.

In those embodiments where the supported lipid bilayer comprises two or more different lipid components, the relative percentages of the two or more different lipid components may be the same or may be different. In one non-limiting example, the supported lipid bilayer may comprise 25% PS, 74.5% PC and 0.5% Lissamine Rhodamine PE. In another non-limiting example, the supported lipid bilayer may comprise 5% PIP, 20% PS, 74.5% PC and 0.5% Lissamine Rhodamine PE. For some types of lipid, the requirements for forming a stable supported lipid bilayer may limit the relative percentage of that lipid in the bilayer to less than 100%. In these cases, the relative percentage of the de-stabilizing lipid component may typically range from about 1% to about 50%. In some embodiments, the relative percentage of the de-stabilizing lipid component in the supported lipid bilayer may be at least about 1%, at least about 5%, at least about 10%, at least about 20%, at least about 30%, at least about 40%, or at least about 50%. In some embodiments, the relative percentage of the de-stabilizing lipid component in the supported lipid bilayer may be at most about 50%, at most about 40%, at most about 30%, at most about 20%, at most about 10%, at most about 5%, or at most about 1%. Those of skill in the art will recognize that the relative percentage of a de-stabilizing lipid component in the supported lipid bilayer may have any value within this range, e.g. about 12.5%.

As indicated above, the supported lipid bilayer may also comprise integral protein components, or subunits or subdomains thereof. In some embodiments, the supported lipid bilayer may also include non-integral protein components that are tethered to the lipid bilayer, e.g. through covalent or non-covalent coupling to a lipid-like or hydrophobic moiety that inserts itself into the lipid bilayer.

In some embodiments, the number of different protein components (integral or non-integral) included in the supported lipid bilayer may range from about 1 to about 10 or more. In some embodiments, the number of different protein components may be at least 1, at least 2, at least 3, at least 4, at least 5, at least 6, at least 7, at least 8, at least 9, or at least 10. In some embodiments, the number of different protein components may be at most 10, at most 9, at most 8, at most 7, at most 6, at most 5, at most 4, at most 3, at most 2, or at most 1.

In some embodiments, the molar fraction of a given protein component of the lipid bilayer may range from about 0.1 to about 1. In some embodiments, the molar fraction of a given protein component may be at least about 0.1, at least about 0.2, at least about 0.3, at least about 0.4, at least about 0.5, at least about 0.6, at least about 0.7, at least about 0.8, at least about 0.9, or at least about 1. In some embodiments, the molar fraction of a given protein component may be at most about 1, at most about 0.9, at most about 0.8, at most about 0.7, at most about 0.6, at most about 0.5, at most about 0.4, at most about 0.3, at most about 0.2, or at most about 0.1. Those of skill in the art will recognize that the molar fraction of a given protein component in the lipid bilayer may have any value within this range, e.g. about 0.15%.

In some embodiments, artificial membranes, e.g. non-lipid based membranes, may be used to attach or tether peripheral membrane proteins and other membrane protein components to the substrate surface. Examples of artificial membranes that may be used include, but are not limited to, polymeric membranes (e.g., cellulose acetate, nitrocellulose, and cellulose esters, polysulfone, polyether sulfone, polyacrilonitrile, polyamide, polyimide, polyethylene and polypropylene, polytetrafluoroethylene, polyvinylidene fluoride, and polyvinylchloride membranes), polymer electrolyte membranes (e.g., ion exchange membranes that have been functionalized by the addition of highly acidic or basic functional groups to a polymer scaffold, e.g., sulfonic acid and quaternary ammonium functional groups, thereby enabling the membrane to form water channels and selectively transport cations or anions), and the like. The use of artificial membranes may confer potential advantages in some embodiments, for example, the ability to tune the hydrophobic/hydrophilic properties of the membrane surface through modification of the polymer backbone, or improved durability.

Tethering of peripheral membrane proteins, other membrane protein components, or other biomolecular components to artificial membranes may require the use of any of a variety of covalent or non-covalent coupling chemistries known to those of skill in the art. Examples of suitable amine-reactive conjugation chemistries that may be used include, but are not limited to, reactions involving isothiocyanate, isocyanate, acyl azide, NHS ester, sulfonyl chloride, aldehyde, glyoxal, epoxide, oxirane, carbonate, aryl halide, imidoester, carbodiimide, anhydride, and fluorophenyl ester groups. Examples of suitable carboxyl-reactive conjugation chemistries include, but are not limited to, reactions involving carbodiimide compounds, e.g., water soluble EDC (1-ethyl-3-(3-dimethylaminopropyl)carbodiimide.HCL). Such conjugation reactions may be performed with or without the use of a suitable linker or spacer molecule to adjust the distance between the membrane and the protein or other molecule being tethered or attached. Examples of non-covalent binding or conjugation chemistries include the use of high-affinity biotin-streptavidin (or strepatavidin analogue) interactions or the use of His-tag/Ni-NTA binding.

Collection Optics and Detector

FIG. 5 further illustrates the collection optics and detector used to detect nonlinear optical signals generated upon sequential illumination of the discrete regions of the substrate. Because surface-selective nonlinear optical techniques are coherent techniques, meaning that the fundamental and nonlinear optical light beams have wave fronts that propagate through space with well-defined spatial and phase relationships, minimal collection optics are required. Emitted nonlinear optical signals are collected by means of a prism (or the integrated prism or grating array of the microplate device described above) and directed via a dichroic reflector and mirror to the detector. Additional optical components, e.g. lenses, optical bandpass filters, mirrors, etc. are optionally used to further shape, steer, and/or filter the beam prior to reaching the detector. A variety of different photodetectors may be used, including but not limited to photodiodes, avalanche photodiodes, photomultipliers, CMOS sensors, or CCD devices.

X-Y Translation Stage

Figure 4:
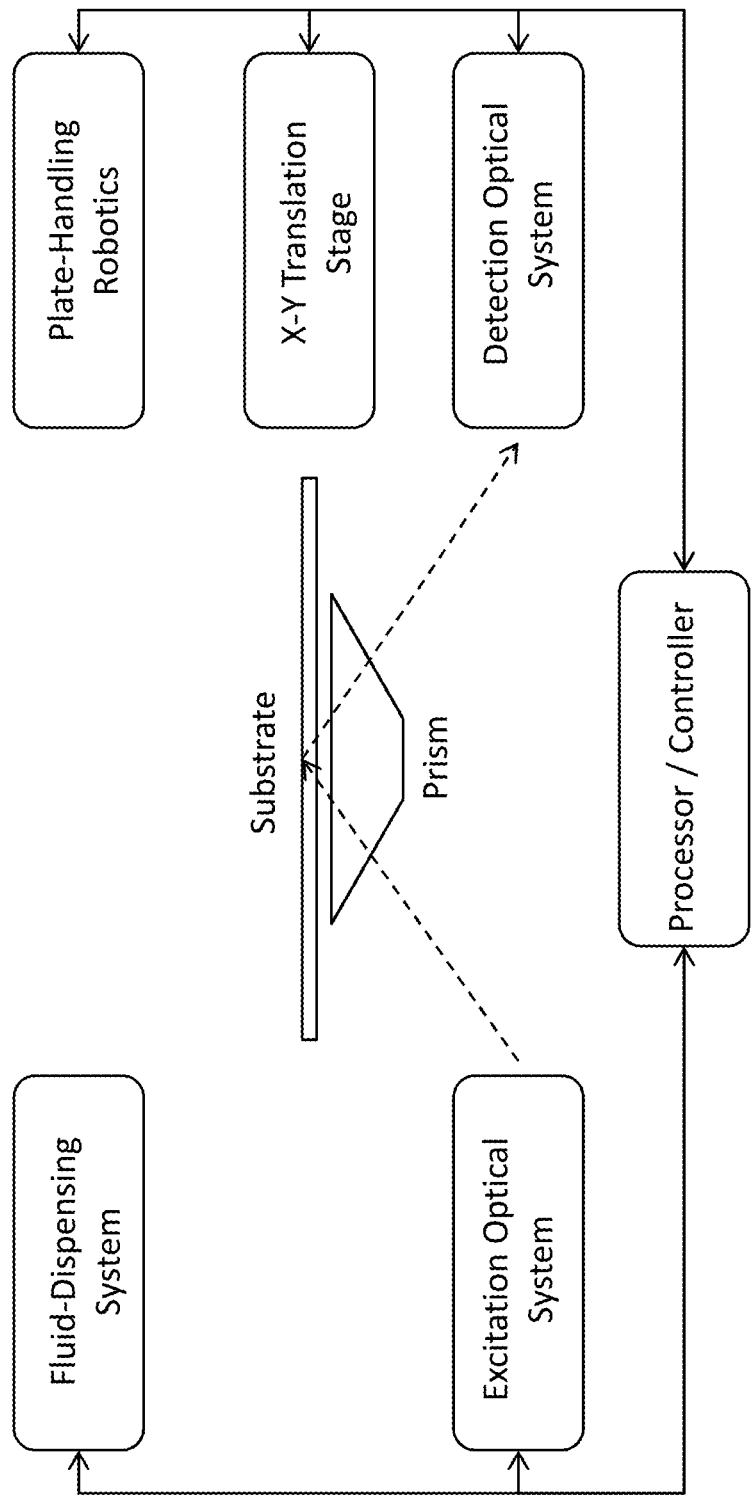
FIG. 4 illustrates one non-limiting example of the system architecture for a high throughput analysis system for determining conformational change in biological molecules, e.g. peripheral membrane proteins or other biological entities, based on nonlinear optical detection.

As illustrated in FIG. 4, implementation of the high throughput systems disclosed herein ideally utilizes a high precision X-Y (or in some cases, an X-Y-Z) translation stage for re-positioning the substrate (in any of the formats described above) in relation to the excitation light beam. Suitable translation stages are commercially available from a number of vendors, for example, Parker Hannifin. Precision translation stage systems typically comprise a combination of several components including, but not limited to, linear actuators, optical encoders, servo and/or stepper motors, and motor controllers or drive units. High precision and repeatability of stage movement is required for the systems and methods disclosed herein in order to ensure accurate measurements of nonlinear optical signals when interspersing repeated steps of optical detection and/or liquid-dispensing. Also, as the size of the focal spot for the excitation light [20-200 microns in diameter or on a side is substantially smaller than the size of the discrete regions on the substrate, in some aspects of the present disclosure, it may also be desirable to return to a slightly different position within a given discrete region when making replicate measurements, or to slowly scan the excitation beam across a portion of the discrete region over the course of a single measurement, thereby eliminating potential concerns regarding the photo-bleaching effects of long exposures or prior exposures.

Consequently, the methods and systems disclosed herein further comprise specifying the precision with which the translation stage is capable of positioning a substrate in relation to the excitation light beam. In one aspect of the present disclosure, the precision of the translation stage is between about 1 um and about 10 um. In other aspects, the precision of the translation stage is about 10 um or less, about 9 um or less, about 8 um or less, about 7 um or less, about 6 um or less, about 5 um or less, about 4 um or less, about 3 um or less, about 2 um or less, or about 1 um or less. Those of skill in the art will appreciate that the precision of the translation stage may fall within any range bounded by any of these values (e.g. from about 1.5 um to about 7.5 um).

Fluid Dispensing System

As illustrated in FIG. 4, some embodiments of the high throughput systems disclosed herein further comprise an automated, programmable fluid-dispensing (or liquid-dispensing) system for use in contacting the biological or target entities immobilized on the substrate surface with test entities (or test compounds), the latter typically being dispensed in solutions comprising aqueous buffers with or without the addition of a small organic solvent component, e.g. dimethylsulfoxide (DMSO). Suitable automated, programmable fluid-dispensing systems are commercially available from a number of vendors, e.g. Beckman Coulter, Perkin Elmer, Tecan, Velocity 11, and many others. In a preferred aspect of the systems and methods disclosed herein, the fluid-dispensing system further comprises a multichannel dispense head, e.g. a 4 channel, 8 channel, 16 channel, 96 channel, or 384 channel dispense head, for simultaneous delivery of programmable volumes of liquid (e.g. ranging from about 1 microliter to several milliliters) to multiple wells or locations on the substrate.

Plate-Handling Robotics

In other aspects of the high throughput systems disclosed herein, the system further comprises a microplate-handling (or plate-handling) robotic system (FIG. 4) for automated replacement and positioning of substrates (in any of the formats described above) in relation to the optical excitation and detection optics, or for optionally moving substrates between the optical instrument and the fluid-dispensing system. Suitable automated, programmable microplate-handling robotic systems are commercially available from a number of vendors, including Beckman Coulter, Perkin Elemer, Tecan, Velocity 11, and many others. In a preferred aspect of the systems and methods disclosed herein, the automated microplate-handling robotic system is configured to move collections of microwell plates comprising immobilized biological entities and/or aliquots of test compounds to and from refrigerated storage units.

Processor/Controller and Constraint-Based Scheduling Algorithm

In another aspect of the present disclosure, the high throughput systems disclosed further comprise a processor (or controller, or computer system) (FIG. 4) configured to run system software which controls the various subsystems described (excitation and detection optical systems, X-Y (or X-Y-Z) translation stage, fluid-dispensing system, and plate-handling robotics) and synchronizes the different operational steps involved in performing high throughput conformational analysis. In addition to handling the data acquisition process, i.e. collection of output electronic signals from the detector that correspond to the nonlinear optical signals associated with conformational change, the processor or controller is also typically configured to store the data, perform data processing and display functions (including determination of whether or not changes in orientation or conformation have occurred for the biological entities, or combinations of biological and test entities, that have been tested), and operate a graphical user interface for interactive control by an operator. The processor or controller may also be networked with other processors, or connected to the internet for communication with other instruments and computers at remote locations.

Typical input parameters for the processor/controller may include set-up parameters such as the total number of microwell plates to be analyzed; the number of wells per plate; the number of times excitation and detection steps are to be performed for each discrete region of the substrate or well of the microplate (e.g. to specify endpoint assay or kinetic assay modes); the total timecourse over which kinetic data should be collected for each discrete region or well; the order, timing, and volume of test compound solutions to be delivered to each discrete region or well; the dwell time for collection and integration of nonlinear optical signals; the name(s) of output data files; and any of a number of system set-up and control parameters known to those skilled in the art.

In a preferred aspect of the present disclosure, the processor or controller is further configured to perform system throughput optimization by means of executing a constraint-based scheduling algorithm. This algorithm utilizes system set-up parameters as described above to determine an optimal sequence of interspersed excitation/detection and liquid-dispensing steps for discrete regions or wells that may or may not be adjacent to each other, such that the overall throughput of the system, in terms of number of biological entities and/or test entities analyzed per hour, is maximized.

Optimization of system operational steps is an important aspect of achieving high throughput analysis. In some aspects of the disclosed methods and systems, the average throughput of the analysis system may range from about 10 test entities tested per hour to about 1,000 test entities tested per hour. In some aspects, the average throughput of the analysis system may be at least 10 test entities tested per hour, at least 25 test entities tested per hour, at least 50 test entities tested per hour, at least 75 test entities tested per hour, at least 100 test entities tested per hour, at least 200 test entities tested per hour, at least 400 test entities tested per hour, at least 600 test entities tested per hour, at least 800 test entities tested per hour, or at least 1,000 test entities tested per hour. In other aspects, the average throughput of the analysis system may be at most 1,000 test entities tested per hour, at most 800 test entities tested per hour, at most 600 test entities tested per hour, at most 400 test entities tested per hour, at most 200 test entities tested per hour, at most 100 test entities tested per hour, at most 75 test entities tested per hour, at most 50 test entities tested per hour, at most 25 test entities tested per hour, or at most 10 test entities tested per hour.

Computer Systems and Networks

In various embodiments, the methods and systems of the invention may further comprise software programs installed on computer systems and use thereof. Accordingly, as noted above, computerized control of the various subsystems and synchronization of the different operational steps involved in performing high throughput conformational analysis, including data analysis and display, are within the bounds of the invention.

Figure 15:
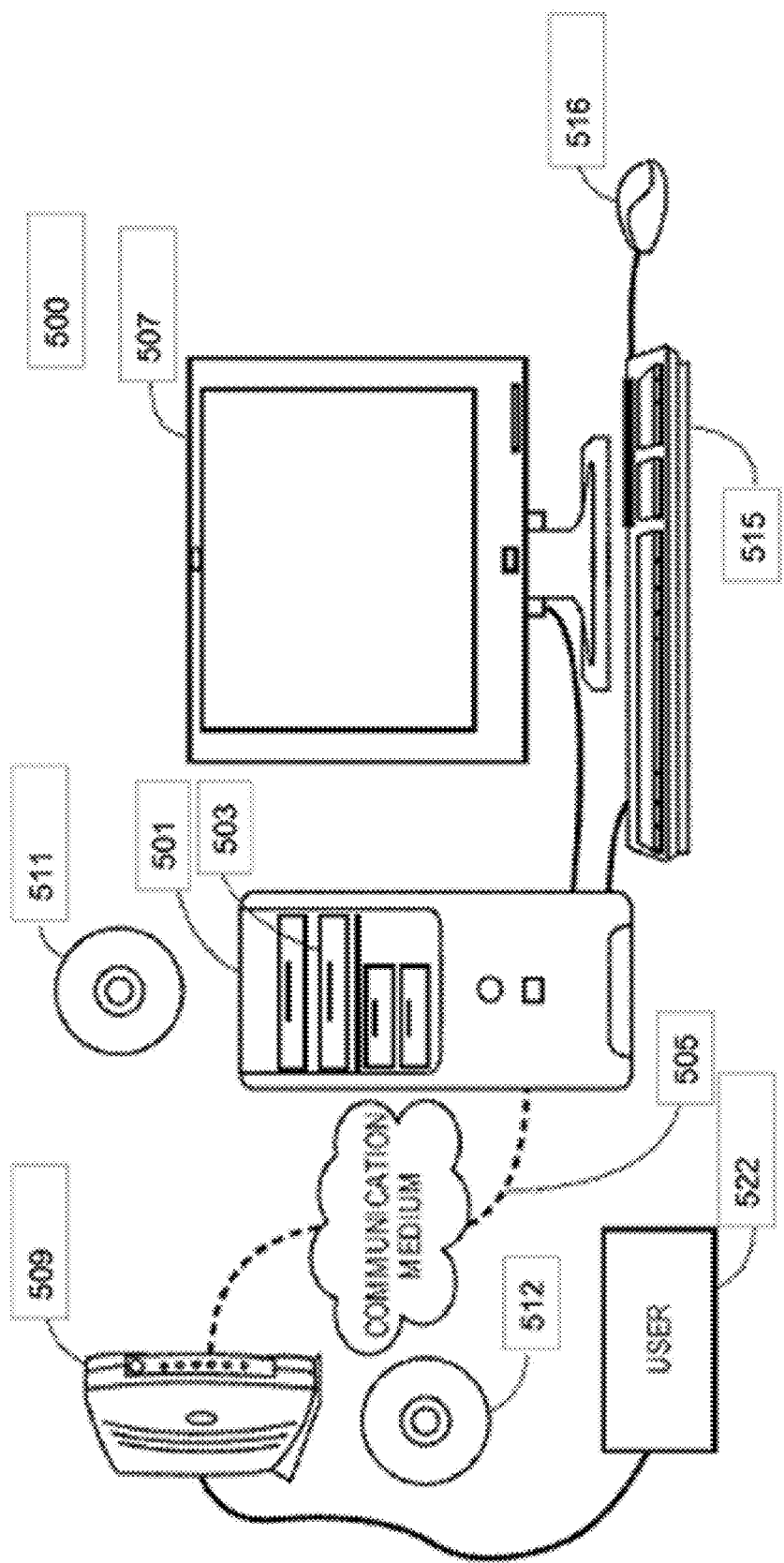
FIG. 15 illustrates a computer system that may be configured to control the operation of the systems disclosed herein.

The computer system 500 illustrated in FIG. 15 may be understood as a logical apparatus that can read instructions from media 511 and/or a network port 505, which can optionally be connected to server 509 having fixed media 512. The system, such as shown in FIG. 15 can include a CPU 501, disk drives 503, optional input devices such as keyboard 515 and/or mouse 516 and optional monitor 507. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 522 as illustrated in FIG. 15.

Figure 16:
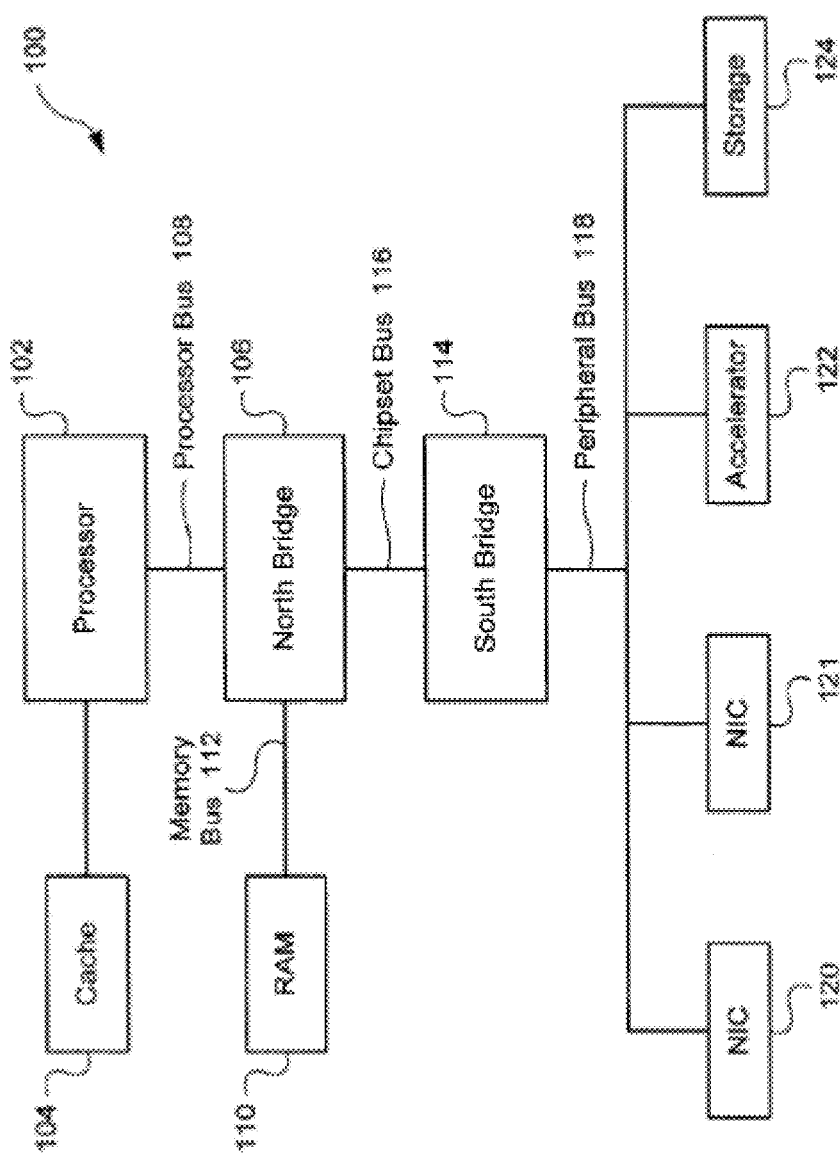
FIG. 16 is a block diagram illustrating a first example architecture of a computer system that can be used in connection with example embodiments of the present invention.

FIG. 16 is a block diagram illustrating a first example architecture of a computer system 100 that can be used in connection with example embodiments of the present invention. As depicted in FIG. 16, the example computer system can include a processor 102 for processing instructions. Non-limiting examples of processors include: the Intel Xeon™ processor, the AMD Opteron™ processor, the Samsung 32-bit RISC ARM 1176JZ(F)-S v1.0™ processor, the ARM Cortex-A8 Samsung S5PC100™ processor, the ARM Cortex-A8 Apple A4™ processor, the Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 16, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MacOS™, BlackBerry OS™, iOS™, and other functionally-equivalent operating systems, as well as application software running on top of the operating system for managing data storage and optimization in accordance with example embodiments of the present invention.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 17:
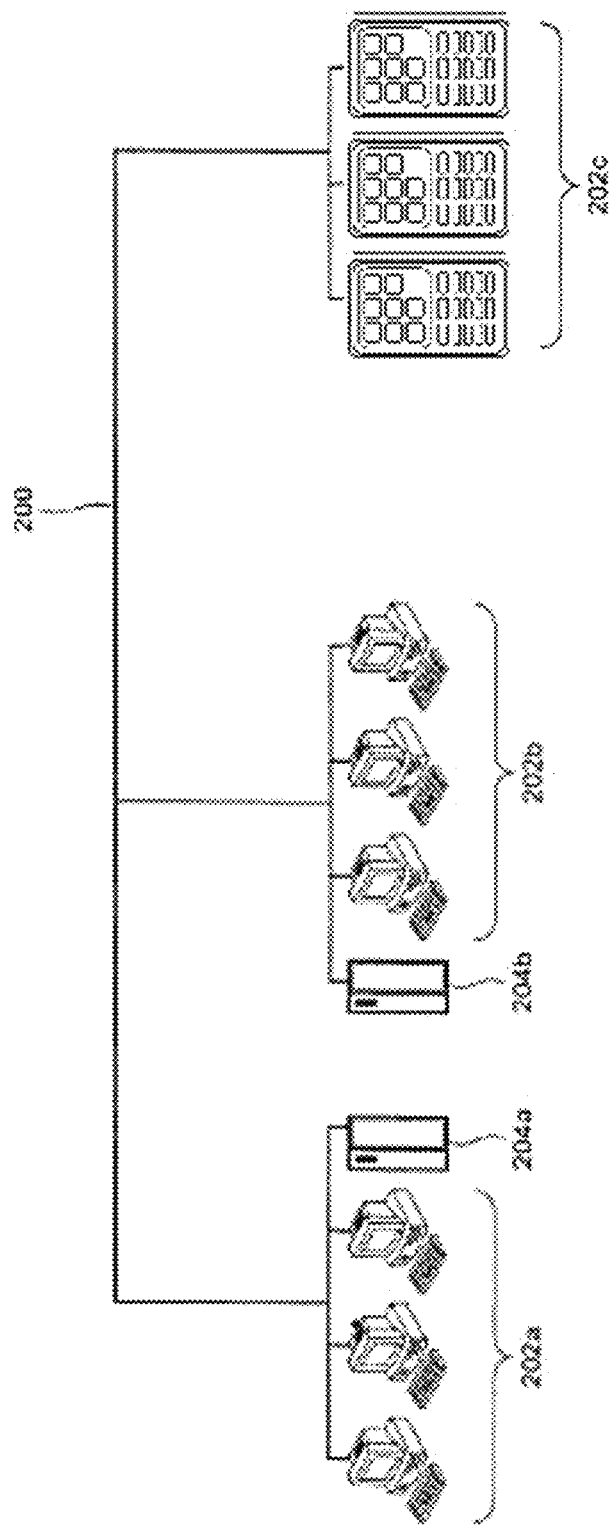
FIG. 17 is a diagram showing one embodiment of a network with a plurality of computer systems, a plurality of cell phones and personal data assistants, and Network Attached Storage (NAS).

FIG. 17 is a diagram showing a network 200 with a plurality of computer systems 202a, and 202b, a plurality of cell phones and personal data assistants 202c, and Network Attached Storage (NAS) 204a, and 204b. In example embodiments, systems 202a, 202b, and 202c can manage data storage and optimize data access for data stored in Network Attached Storage (NAS) 204a and 204b. A mathematical model can be used for the data and be evaluated using distributed parallel processing across computer systems 202a, and 202b, and cell phone and personal data assistant systems 202c. Computer systems 202a, and 202b, and cell phone and personal data assistant systems 202c can also provide parallel processing for adaptive data restructuring of the data stored in Network Attached Storage (NAS) 204a and 204b. FIG. 17 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 18:
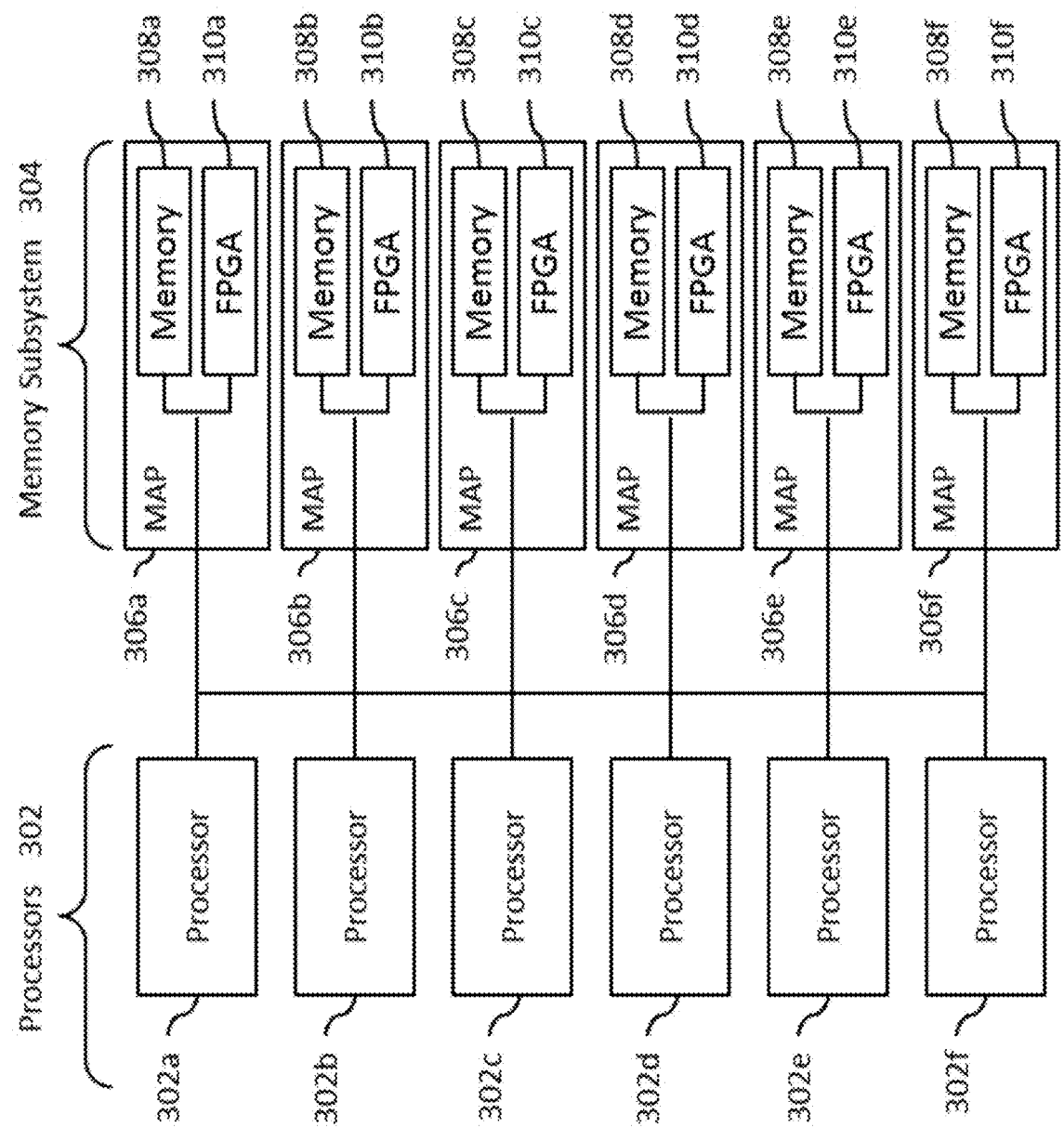
FIG. 18 is a block diagram of a multiprocessor computer system using a shared virtual address memory space in accordance with an example embodiment.

FIG. 18 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 18, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 16.

EXAMPLE 1

Binding of Peripheral Membrane Proteins to PI4P Bilayers

Figure 12:
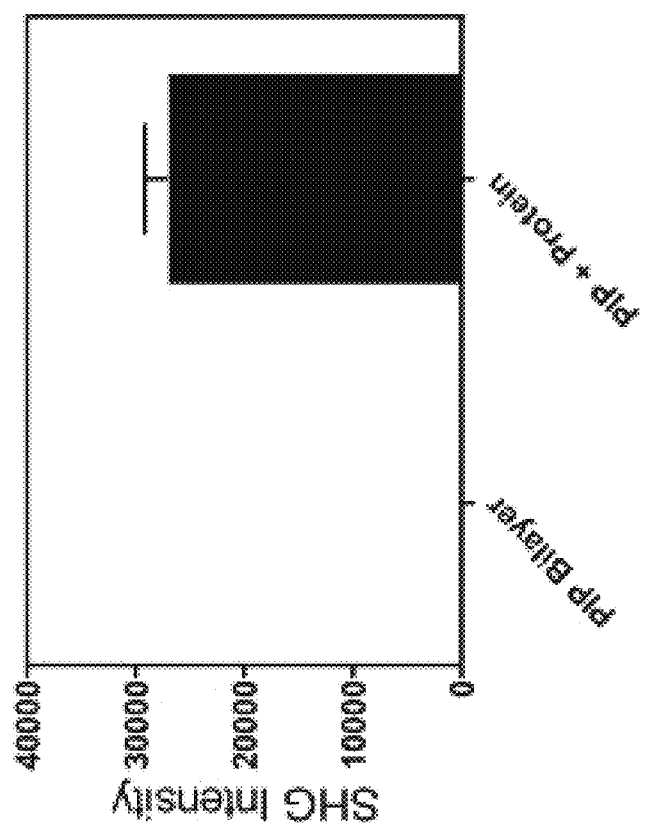
FIG. 12 provides an example of data for SHG detection of the binding of a peripheral membrane protein labeled with SHG-1 SE dye (Biodesy, Inc., South San Francisco, Calif.) to a phosphatidylinositol-4-phosphate (PI4P) bilayer (74.5% DOPC, 25% PI4P, 0.5% Lissamine Rhodamine PE) relative to the signal for a bilayer-only control.

FIG. 12 shows an example of data for SHG detection of peripheral membrane protein binding to a supported lipid bilayer comprising phosphatidylinositol-4-phosphate. A solution of small unilamellar vesicles (SUVs) containing phosphatidylinositol-4-phosphate (final lipid bilayer composition: 74.5% DOPC, 25% PI4P, 0.5% Lissamine Rhodamine PE) was prepared using standard laboratory techniques. The SUVs were diluted five-fold in tris-buffered saline, and calcium chloride was added to final concentration of 5 mM. The diluted SUVs were deposited onto a glass-bottom microtiter plate comprising custom integrated optics and allowed to incubate for a minimum of thirty minutes to form a supported lipid bilayer. After incubation, excess SUVs were removed by washing ten times with 50 µL of assay buffer containing 20 mM Hepes, pH 8.0, 200 mM NaCl, and 0.005% Tween-20. For this experiment, a full length peripheral membrane protein was obtained from a collaborator and labeled with SHG-1 SE dye (Biodesy, Inc., South San Francisco, Calif.) using amine-reactive succinimidyl ester conjugation chemistry. After washing to remove excess SUVs, a 2 µM labeled protein solution was prepared in assay buffer and the protein was deposited at a 1:1 volume ratio to buffer in the well to produce a final concentration of 1 µM protein in the well. The protein was then allowed to incubate overnight at 4 C. After an overnight incubation, excess protein was removed by washing five times with assay buffer. The plate was then placed on the detection instrument and the SHG intensity in each well was determined.

Figure 13:
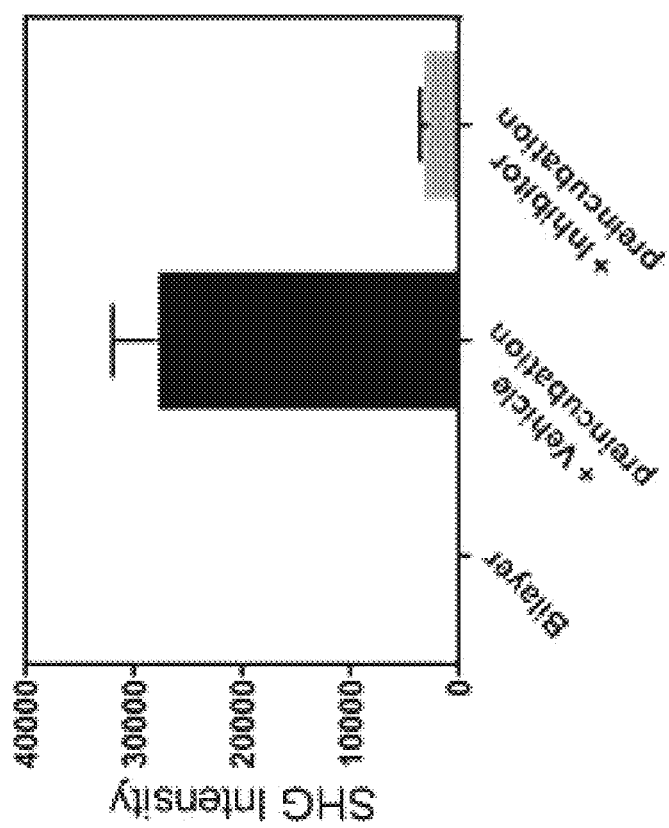
FIG. 13 provides an example of data for SHG detection of the binding of a peripheral membrane protein labeled with SHG-1 SE dye (Biodesy, Inc., South San Francisco, Calif.) to a phosphatidylinositol-4-phosphate (PI4P) bilayer (74.5% DOPC, 25% PI4P, 0.5% Lissamine Rhodamine PE) relative to the signals for a bilayer-only control and for blocking of binding to the membrane by an inhibitor.

FIG. 13 shows an example of data demonstrating blocking of specific binding of the peripheral membrane protein to the PI4P bilayer by pre-incubating with a known inhibitor. For this experiment, the SUV deposition and washing steps were performed as described above. However, prior to protein deposition, the peripheral membrane protein sample was incubated for thirty minutes on ice with either 20 µM of the inhibitor or DMSO as the vehicle control. Protein samples were deposited into each well as above with a 1 µM final concentration of protein and a 10 µM final concentration of inhibitor. After overnight incubation at 4 C, samples were washed in assay buffer+1% DMSO and read on the SHG detection instrument as described above.

EXAMPLE 2

Binding of Peripheral Membrane Proteins to Ni-NTA/PS Bilayers

Figure 14:
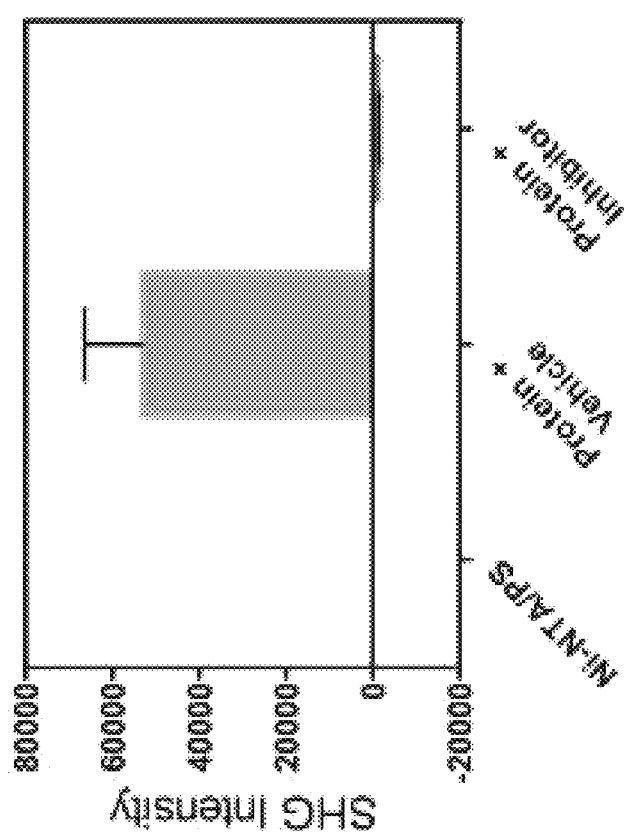
FIG. 14 provides an example of data for SHG detection of the binding of a labeled peripheral membrane protein to a NTA-phosphatidylserine (NTA-PS) bilayer (64.5% DOPC, 25% PS, 10% Ni-NTA, 0.5% Lissamine Rhodamine PE) relative to the signals for a bilayer-only control and for blocking of binding to the membrane by an inhibitor.

FIG. 14 shows an example of data for SHG detection of a labeled peripheral membrane protein binding to a supported lipid bilayer comprising Ni-NTA-phosphatidylserine (Ni-NTA/PS). The preparation of supported lipid bilayers (final lipid bilayer composition: 64.5% DOPC, 25% PS, 10% Ni-NTA, 0.5% Lissamine Rhodamine PE) and the binding assay protocol were as described above. Again the data demonstrate blocking of specific binding of the peripheral membrane protein to the Ni-NTA/PS bilayer by pre-incubating with a known inhibitor.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for detecting binding of a candidate peripheral membrane protein to a supported membrane, the method comprising:
   a) providing a substrate having a first substrate surface comprising a supported membrane, wherein the supported membrane comprises one or more lipid or protein components;
   b) contacting the supported membrane with the candidate peripheral membrane protein, wherein the candidate peripheral membrane protein is labeled with a nonlinear-active label;
   c) illuminating the first substrate surface with excitation light of at least one fundamental frequency, wherein the excitation light is provided by at least one light source; and
   d) detecting light generated by the nonlinear-active label as a result of the illumination in step c) both before and after contacting the supported membrane with the candidate peripheral membrane protein, wherein a change in a physical property of the light detected before and after contacting the supported membrane with the candidate peripheral membrane protein indicates that the candidate peripheral membrane protein binds to the supported membrane or a component thereof;
   wherein the candidate peripheral membrane protein is a protein comprising a subdomain selected from the group consisting of C1 domains, C2 domains, PX domains, Fab1 domains, YOTB domains, Vac1 domains, EEA1 domains, FYVE domains, ENTH domains, ANTH domains, BAR domains, FERM domains, PDZ domains, Tubby domains, or any combination thereof.

2. The method of claim 1, wherein the supported membrane comprises a supported lipid bilayer.

3. The method of claim 1, further comprising adjusting the relative percentages of two or more lipid components in the supported lipid bilayer to enhance the degree of binding of the peripheral membrane protein to the supported lipid bilayer.

4. The method of claim 1, wherein the supported membrane comprises an artificial membrane.

5. The method of claim 4, wherein the artificial membrane has been modified by attachment of one or more lipid, protein, or membrane protein components.

6. The method of claim 1, wherein the light generated by the nonlinear-active label is coherent.

7. The method of claim 1, wherein the nonlinear-active label comprises a second harmonic-active, sum frequency-active, or difference frequency-active label.

8. The method of claim 1, wherein the one or more nonlinear-active labels are nonlinear-active unnatural amino acids that have been incorporated into the peripheral membrane protein.

9. The method of claim 1, wherein the first substrate surface comprises an array of supported lipid bilayers or artificial membranes localized in discrete regions of the first substrate surface.

10. The method of claim 2, wherein one or more lipid components of the supported lipid bilayer comprise lipids selected from the group consisting of diacylglycerol, phosphatidic acid (PA), phosphatidylethanolamine (PE), phosphatidylcholine (PC), phosphatidylserine (PS), phosphatidylinositol (PI), phosphatidylinositol phosphate (PIP), phosphatidylinositol biphosphate (PIP2), phosphatidylinositol triphosphate (PIP3), ceramide phosphorylcholine (sphingomyelin; SPH), ceramide phosphorylethanolamine (sphingomyelin; Cer-PE), ceramide phosphoryllipid, cholesterol, or any combination thereof.

11. The method of claim 2, wherein one or more protein components of the supported lipid bilayer comprise proteins or subdomains thereof selected from the group consisting of G-protein coupled receptors (GPCRs), transmembrane receptors, receptor tyrosine kinases, ion channel proteins, cytochrome P450 enzymes (CYPs), transport proteins, photosynthetic reaction centers, lipid-anchored proteins, or any combination thereof.

12. The method of claim 1, wherein the candidate peripheral membrane protein or a subdomain thereof is selected from the group consisting of extracellular matrix proteins, protein kinases, transmembrane receptor regulatory proteins, ion channel regulatory proteins, cytochrome proteins, lipid-anchored proteins, or any combination thereof.

13. The method of claim 1, wherein the peripheral membrane protein is contacted with a test agent prior to or simultaneously with contacting the supported lipid bilayer or artificial membrane with the peripheral membrane protein.

14. The method of claim 1, wherein the peripheral membrane protein is contacted with a test agent after contacting the supported lipid bilayer or artificial membrane with the peripheral membrane protein.

15. The method of claim 1, further comprising comparing the change in a physical property of the detected light observed upon contacting the peripheral membrane protein with a test agent to that observed upon contacting the peripheral membrane protein with a control.

16. The method of claim 1, wherein one or more lipid components or one or more protein components of the supported lipid bilayer or artificial membrane are also labeled with a nonlinear-active label.

17. The method of claim 1, wherein one or more lipid components or one or more protein components are labeled with a nonlinear-active label that is the same as that used to label the peripheral membrane protein.

18. The method of claim 1, wherein one or more lipid components or one or more protein components are labeled with a nonlinear-active label that is different from that used to label the peripheral membrane protein.

* * * * *